United States Patent
Aradottir et al.

(10) Patent No.: US 11,373,746 B2
(45) Date of Patent: Jun. 28, 2022

(54) BASAL TITRATION WITH ADAPTIVE TARGET GLUCOSE LEVEL

(71) Applicant: Novo Nordisk A/S, Bagsvaerd (DK)

(72) Inventors: Tinna Bjoerk Aradottir, Copenhagen (DK); Henrik Bengtsson, Taastrup (DK); Pete Brockmeier, Copenhagen V (DK)

(73) Assignee: Novo Nordisk A/S, Bagsvaerd (DK)

( * ) Notice: Subject to any disclaimer, the term of this patent is extended or adjusted under 35 U.S.C. 154(b) by 843 days.

(21) Appl. No.: 16/316,237

(22) PCT Filed: Jun. 23, 2017

(86) PCT No.: PCT/EP2017/065578
§ 371 (c)(1),
(2) Date: Jan. 8, 2019

(87) PCT Pub. No.: WO2018/007172
PCT Pub. Date: Jan. 11, 2018

(65) Prior Publication Data
US 2019/0147999 A1    May 16, 2019

(30) Foreign Application Priority Data
Jul. 8, 2016 (EP) .................................. 16178554

(51) Int. Cl.
*G16H 20/17* (2018.01)
*A61B 5/145* (2006.01)
(Continued)

(52) U.S. Cl.
CPC ........... *G16H 20/17* (2018.01); *A61B 5/0022* (2013.01); *A61B 5/14532* (2013.01);
(Continued)

(58) Field of Classification Search
CPC .... G16H 20/17; G16H 50/20; A61B 5/14532; A61M 5/14244; A61M 38/28; A61M 5/1723
See application file for complete search history.

(56) References Cited

U.S. PATENT DOCUMENTS 5,971,922 A    10/1999 Arita et al.
7,651,845 B2    1/2010 Doyle, III et al.
(Continued)

FOREIGN PATENT DOCUMENTS

AU    2015/100005 A4    2/2015
CN    102016855 A    4/2011
(Continued)

*Primary Examiner* — Manuel A Mendez
(74) *Attorney, Agent, or Firm* — Wesley Nicolas

(57) ABSTRACT

Systems and methods are provided for adjusting long acting insulin medicament dosages for a subject. A plurality of timestamped glucose measurements of the subject and insulin injection data is obtained. A first glycaemic risk measures is determined, where the first risk glycaemic risk measure is i) glucose level variability across the glucose measurements, (ii) a variability in fasting glucose levels calculated from the glucose measurements, (iii) a minimum observed glucose measurement in the plurality of glucose measurements (iv) rate of change in ISF, or (v) adherence values. A fasting blood glucose target function is computed based upon at least the first glycaemic risk measure thereby obtaining an updated target fasting blood glucose level that is between a minimum and maximum target fasting blood glucose level. The long acting insulin medicament dosage is adjusted based upon the updated target fasting blood glucose level.

15 Claims, 15 Drawing Sheets

(51) Int. Cl.
*G16H 40/63* (2018.01)
*G16H 50/30* (2018.01)
*A61B 5/00* (2006.01)
*G16H 50/20* (2018.01)
*A61M 5/20* (2006.01)

(52) U.S. Cl.
CPC .......... *A61B 5/4839* (2013.01); *A61B 5/7275* (2013.01); *A61M 5/20* (2013.01); *G16H 40/63* (2018.01); *G16H 50/20* (2018.01); *G16H 50/30* (2018.01); *A61M 2005/2093* (2013.01); *A61M 2205/3306* (2013.01); *A61M 2205/3592* (2013.01); *A61M 2205/50* (2013.01); *A61M 2205/52* (2013.01); *A61M 2205/581* (2013.01); *A61M 2205/6054* (2013.01); *A61M 2230/005* (2013.01); *A61M 2230/201* (2013.01); *A61M 2230/50* (2013.01)

(56) References Cited

U.S. PATENT DOCUMENTS

| | | |
|---|---|---|
| 8,370,077 B2 | 2/2013 | Bashan et al. |
| 8,562,587 B2 | 10/2013 | Kovatchev et al. |
| 10,525,199 B2 | 1/2020 | Guerrini |
| 2005/0272640 A1 | 12/2005 | Doyle et al. |
| 2010/0125241 A1 | 5/2010 | Prud'homme et al. |
| 2010/0292634 A1 | 11/2010 | Kircher, Jr. et al. |
| 2011/0313674 A1 | 12/2011 | Duke et al. |
| 2013/0245547 A1 | 9/2013 | El-Khatib et al. |
| 2014/0180240 A1 | 6/2014 | Finan et al. |
| 2014/0187887 A1 | 7/2014 | Dunn et al. |
| 2015/0190098 A1 | 7/2015 | Patek et al. |

FOREIGN PATENT DOCUMENTS

| | | |
|---|---|---|
| CN | 102334113 A | 1/2012 |
| CN | 103907116 A | 7/2014 |
| CN | 105339943 A | 2/2016 |
| CN | 105592779 A | 5/2016 |
| EP | 1281351 A2 | 2/2003 |
| JP | H11296598 A | 10/1999 |
| JP | 2008510542 A | 4/2008 |
| JP | 2011518634 A | 6/2011 |
| JP | 2014514120 A | 6/2014 |
| WO | 2005/000209 A2 | 1/2005 |
| WO | 2006021430 | 3/2006 |
| WO | 07116226 A2 | 10/2007 |
| WO | 2009001349 A1 | 12/2008 |
| WO | 2009133558 | 11/2009 |
| WO | 2009146445 | 12/2009 |
| WO | 2010089306 A1 | 8/2010 |
| WO | 2012152628 | 11/2012 |
| WO | 2013184896 A1 | 12/2013 |
| WO | 2014029810 A2 | 2/2014 |
| WO | 2014145335 A1 | 9/2014 |
| WO | 2015021041 A2 | 2/2015 |

— 402

Methods for autonomously adjusting a long acting insulin medicament dosage 216 in a prescribed insulin regimen for a subject using a device 250 are provided. The device has a first data structure 210 that includes the prescribed insulin regimen 212 which includes a basal insulin medicament dosage regimen 214. The basal insulin medicament dosage regimen specifies the long acting insulin medicament dosage. The first data structure 210 specifies an original target fasting blood glucose level 226 used as a basis to compute the long acting insulin medicament dosage. A first data set 228 is obtained. The first data set comprises a plurality of glucose measurements of the subject taken over a time course and, for each respective glucose measurement 230 in the plurality of glucose measurements, a corresponding timestamp 232 representing when in the time course the respective glucose measurement was made.

— 404

> Successive measurements in the plurality of glucose measurements are autonomously taken from the subject at an interval rate of 5 minutes or less, 3 minutes or less, or 1 minute or less.

— 406

Update a first glycaemic risk measure 236 of the subject. The first glycaemic risk measure is: (i) a total glucose variability observed across the plurality of glucose measurements, (ii) a variability in a plurality of fasting glucose levels calculated from the plurality of glucose measurements, or (iii) a minimum glucose measurement observed in the plurality of glucose measurements.

— 408

> The first data structure further comprises an indication 218 as to when the subject is to inject the long acting insulin medicament dosage. A second data set 238 is obtained from one or more insulin pens 104 used by the subject to apply the prescribed insulin regimen. The second data set comprises medicament records over the time course. Each record 240 comprises: (i) an insulin medicament injection event 242 for an insulin medicament injection using an insulin pen and (ii) a corresponding electronic timestamp 244 that is automatically generated by the respective pen upon occurrence of the event. The fasting blood glucose target function is based upon at least the first glycaemic risk measure and a second glycaemic risk measure, where the first glycaemic risk measure and the second glycaemic risk measure are each independently one or more of: any of the risk measures (i), (ii), (iii) of block 406, (iv) a rate of change in an insulin sensitivity factor calculated using the plurality of glucose measurements and the second data set, or (v) a basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course.

410 — The device further comprises a wireless receiver 284, and the first data set is obtained wirelessly from a glucose sensor 102 affixed to the subject and/or the second data set is obtained wirelessly from the one or more insulin pens 104.

412 — A glycaemic risk measure is the total glucose variability observed across the plurality of glucose measurements computed as one of (i), (ii), (iii), or (iv):
  (i) a range of total glucose levels in the plurality of glucose levels,
  (ii) an interquartile range of glucose levels in the plurality of glucose levels,
  (iii) an average squared difference of the glucose levels in the plurality of glucose levels from the mean ($\mu$) of the plurality of glucose levels ($\sigma^2$) computed as:

$$\sigma^2 = \frac{\sum_i^P (m_i - \mu)^2}{P}$$

where, $m_i$ is the $i^{th}$ glucose levels in the plurality of glucose levels, and P is the number of glucose levels in the plurality of glucose levels, and
  (iv) the standard deviation of the glucose levels in the plurality of glucose levels computed as $\sqrt{\sigma^2}$.

414 — A glycaemic risk measure is the variability in the plurality of fasting glucose levels calculated from the plurality of glucose measurements computed as one of (i), (ii), (iii), or (iv):
  (i) a range of fasting glucose levels in the plurality of fasting glucose levels,
  (ii) an interquartile range of fasting glucose levels in the plurality of fasting glucose levels,
  (iii) an average squared difference of the fasting glucose levels in the plurality of fasting glucose levels from the mean ($\mu$) of the plurality of fasting glucose levels ($\sigma^2$) computed as:

$$\sigma^2 = \frac{\sum_i^P (m_i - \mu)^2}{P}$$

where, $m_i$ is the $i^{th}$ fasting glucose levels in the plurality of fasting glucose levels, and P is the number of fasting glucose levels in the plurality of fasting glucose levels, and
  (iv) the standard deviation of the fasting glucose levels in the plurality of fasting glucose levels computed as $\sqrt{\sigma^2}$.

```
                                                              ┌─ 416
┌─────────────────────────────────────────────────────────────┴───┐
│ Compute a fasting blood glucose target function that is based upon at least the │
│ first glycaemic risk measure thereby obtaining an updated target fasting blood │
│ glucose level that is between the minimum target fasting blood glucose level   │
│ (226) and the maximum target fasting blood glucose level (227). │
```

A range of possible values for the first glycaemic risk measure and a range of possible values for the second glycaemic risk measure are each dimensions of an N-dimensional space ($\mathbb{R}^N$) and the fasting blood glucose target function has the form $\sum_{i}^{N-1} c_i x_i = c_R$ where, $c_i$ is an $i^{th}$ constant applied to an $x_i^{th}$ glycaemic risk measure, the $x_i^{th}$ glycaemic risk measure is in a plurality of glycaemic risk measures that includes the first glycaemic risk measure and the second glycaemic risk measure, i is an integer between one and N-1, and FGL is the target fasting blood glucose level.

The fasting blood glucose target function is based upon a first glycaemic risk measure and a second glycaemic risk measure where the first glycaemic risk measure is the variability in the plurality of fasting glucose levels and the second glycaemic risk measure is the basal adherence score over the time course. A range of possible values for the first glycaemic risk measure and a range of possible values for the second glycaemic risk measure are each dimensions of an n-dimensional space ($\mathbb{R}^N$) and the fasting blood glucose target function has the form:

$$c_1 x_1 + c_2 x_2 = FGL$$

where $c_1$ is a constant applied to the first glycaemic risk measure, $c_2$ is a constant applied to the second glycaemic risk measure, and FGL is the target fasting blood glucose level that is determined.

Fig. 4C

416 (cont.)

422

The first glycaemic risk measure is the variability in the plurality of fasting glucose levels, the second glycaemic risk measure is the basal adherence score over the time course, and a third glycaemic risk measure is the minimum glucose measurement in the plurality of glucose measurements of the subject. The fasting blood glucose target function is a function of: (i) the variability in the plurality of fasting glucose levels as a first dimension of the n-dimensional space, (ii) the basal adherence score over the time course as a second dimension of the n-dimensional space, and (iii) and the minimum glucose measurement in the plurality of glucose measurements of the subject as a third dimension of the n-dimensional space.

424

A range of possible values for the variability in the plurality of fasting glucose levels, a range of possible values for the basal adherence score, and a range of possible values for the minimum glucose measurement define a three dimensional space and the fasting blood glucose target function has the form $c_1 x + c_2 y + c_3 z = FGL$ where $c_1$, $c_2$ and $c_3$ are constants respectively applied to the variability in the plurality of fasting glucose levels, the basal adherence score over the time course, and the minimum glucose measurement, and FGL is the target fasting blood glucose level.

426

The method further comprises storing the new target fasting blood glucose level as the original target fasting blood glucose level in the first data structure. Further, the method is repeated on a recurring basis.

428

Autonomously obtain one or more physiological measurements of the subject. The fasting blood glucose target function is based upon at least the first glycaemic risk measure and a second glycaemic risk measure, where the first glycaemic risk measure and the second glycaemic risk measure are each independently: (i) a total glucose level variability observed across the plurality of glucose measurements, (ii) a variability in the plurality of fasting glucose levels calculated from the plurality of glucose measurements, (iii) the minimum glucose measurement observed in the plurality of glucose measurements, or (iv) the one or more physiological measurements of the subject. Optionally, each physiological measurement 247 in the one or more physiological measurements is a body temperature of the subject or a measurement of cardiovascular activity of the subject.

Fig. 4D

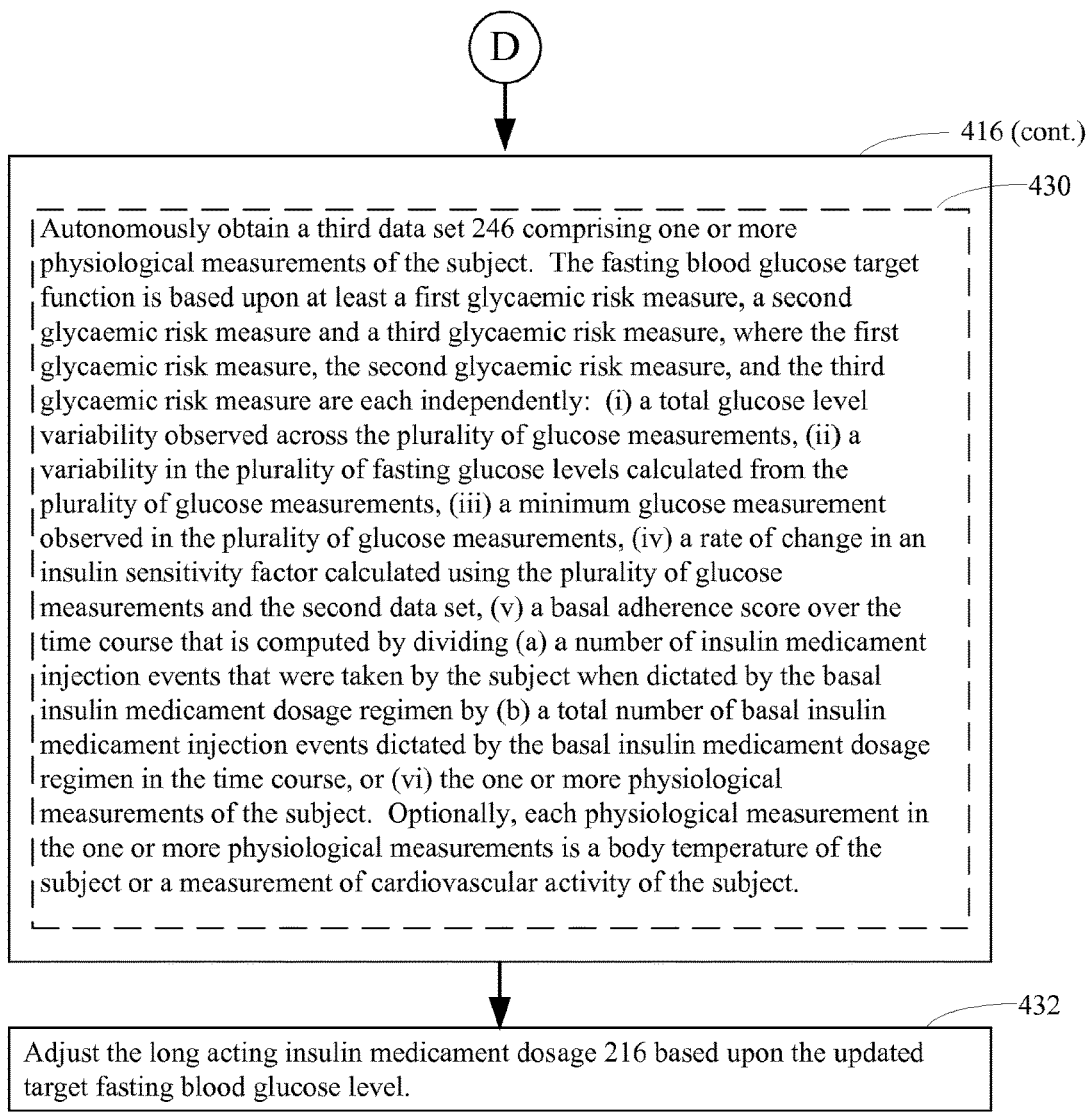

```
                                                    416 (cont.)
                                                    430
```

Autonomously obtain a third data set 246 comprising one or more physiological measurements of the subject. The fasting blood glucose target function is based upon at least a first glycaemic risk measure, a second glycaemic risk measure and a third glycaemic risk measure, where the first glycaemic risk measure, the second glycaemic risk measure, and the third glycaemic risk measure are each independently: (i) a total glucose level variability observed across the plurality of glucose measurements, (ii) a variability in the plurality of fasting glucose levels calculated from the plurality of glucose measurements, (iii) a minimum glucose measurement observed in the plurality of glucose measurements, (iv) a rate of change in an insulin sensitivity factor calculated using the plurality of glucose measurements and the second data set, (v) a basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course, or (vi) the one or more physiological measurements of the subject. Optionally, each physiological measurement in the one or more physiological measurements is a body temperature of the subject or a measurement of cardiovascular activity of the subject.

432

Adjust the long acting insulin medicament dosage 216 based upon the updated target fasting blood glucose level.

Fig. 4E

BASAL TITRATION WITH ADAPTIVE TARGET GLUCOSE LEVEL

CROSS-REFERENCE TO RELATED APPLICATIONS

This application is a 35 U.S.C. § 371 National Stage application of International Application PCT/EP2017/065578 (published as WO 2018/007172), filed Jun. 23, 2017, which claims priority to European Patent Application 16178554.8, filed Jul. 8, 2016, the contents of all above-named applications are incorporated herein by reference.

TECHNICAL FIELD

The present disclosure relates generally to systems and methods for assisting patients and health care practitioners in managing insulin treatment to diabetes, in which prescribed basal injections are titrated based on data sets of blood glucose or continuous glucose, where a target fasting blood glucose target is adapted to estimated risk of hypo- and hyperglycaemia.

BACKGROUND

Type 2 diabetes mellitus is characterized by progressive disruption of normal physiologic insulin secretion. In healthy individuals, basal insulin secretion by pancreatic β cells occurs continuously to maintain steady glucose levels for extended periods between meals. Also in healthy individuals, there is prandial secretion in which insulin is rapidly released in an initial first-phase spike in response to a meal, followed by prolonged insulin secretion that returns to basal levels after 2-3 hours.

Insulin is a hormone that binds to insulin receptors to lower blood glucose by facilitating cellular uptake of glucose, amino acids, and fatty acids into skeletal muscle and fat and by inhibiting the output of glucose from the liver. In normal healthy individuals, physiologic basal and prandial insulin secretions maintain euglycemia, which affects fasting plasma glucose and postprandial plasma glucose concentrations. Basal and prandial insulin secretion is impaired in Type 2 diabetes and early post-meal response is absent. To address these adverse events, patients with Type 2 diabetes are provided with insulin medicament treatment regimens. Patients with Type 1 diabetes are also provided with insulin medicament treatment regimens. The goal of these insulin medicament treatment regimens is to maintain a desired fasting blood glucose target level that will minimize estimated risk of hypo- and hyperglycaemia.

Smart titrators with adjustable step size and physiological parameter estimation and predefined fasting blood glucose target values have been developed to administer insulin medicament treatment regimens.

U.S. Pat. No. 8,370,077 B2 entitled "System for Optimizing A Patient's Inulin Dosage Regimen" to Hygieia, Inc. discloses a system for optimizing a patient's insulin dosage regimen over time in which inputs corresponding at least to one or more components in a patient's present insulin dosage regimen, and data inputs corresponding at least to the patient's blood-glucose-level measurements determined at a plurality of times.

From the data inputs corresponding to the patient's blood-glucose-level measurements, determined at a plurality of times, a determination is made as to whether and by how much to vary at least one of the one or more components in the patient's present insulin dosage regimen in order to maintain the patient's future blood-glucose-level measurements within a predefined range.

U.S. Pat. No. 7,651,845 B2 entitled "Method and Apparatus for Glucose Control and Insulin Dosing for Diabetics" to The Regents of the University of California discloses a computer implemented method and associated apparatus for the combined control of insulin bolus dosing and basal delivery for the goal of achieving normal glycemic response to meals, exercise, stressors, and other perturbations to blood glucose levels. In the disclosure, a run-to-run algorithm is used to monitor blood glucose levels and adjust insulin delivery as conditions are varied.

International Publication Number WO2005000209 A2 entitled "An Improved Method and Apparatus for Dosing Single and Multi-Agent Therapy" to Dimensional Dosing Systems, Inc., discloses a method and apparatus for dosing single and multi-agent therapy, in which a nonlinear technology is used to describe the biological process of dose titration to calculate next agent doses in single and multi-agent therapy. The overall proportion of each agent is determined by the amount of agent as it relates to the dosing range. The overall proportion as well as the intrinsic potency of the agent is used to determine the total proportional effect that each agent has on the surrogate marker. This parameter is then inserted into a four parameter equation for calculating dose by adjusting the proportional change in marker that is attributed to the activity of the agent.

The above-disclosed titrators typically titrate to a predefined target, usually decided by a health care practitioner. This target is chosen with respect to estimated insulin sensitivity and other factors determined in the clinic. Therefore, the target is not updated between visits to the health care practitioner based upon changes in physiological parameters, unexpected responsiveness to the drug or level of adherence, even though these are factors that affect the treatment outcome.

An example where this is a problem is when a basal dose has been forgotten, in other words, insulin regimen adherence is low. In such instances, the titrator should not respond to high glucose measurements by increasing the basal insulin medicament dose to reach the predefined glucose target of the subject that has been set by the health care practitioner during the last visit to the health care practitioner. This could cause overdosing and hypoglycaemia. FIG. 6 illustrates. The top panel of FIG. 6 shows blood glucose concentration during basal titration over forty days. The basal titration algorithm is similar to the one defined in U.S. Pat. No. 8,370,077 B2, with a constant target. As FIG. 6 bottom panel illustrates, the patient occasionally forgets a basal injection, which is not introduced to the basal titrator, leading to hypoglycaemic events (e.g., glucose concentration below 4 mmol/L).

Another situation arises when glucose measurements are wrong, due to some unexplained reasons. In such instances, the titrator should not respond to these extreme measurements by increasing or decreasing the dose proportionally to reach the predefined target. FIG. 7 illustrates. FIG. 7 provides a simulation of a titrator that is titrating a patient over a 40 day period. Every few days the fasting glucose measurement is fifty percent too high due to some unknown reasons. The top panel of FIG. 7 shows blood glucose concentration during basal titration over the 40 days. The basal titration algorithm is similar to the one defined in U.S. Pat. No. 8,370,077 B2, with constant target. As FIG. 7 illustrates, the use of a constant target blood glucose concentration by the titrator leads to hypoglycaemic events (e.g., glucose concentration below 4 mmol/L) in this situation as well. Thus, the titrator should not respond to these extreme measurements by increasing or decreasing the dose proportionally to reach the predefined target.

US 2011/0313674 describes a testing method for optimizing titration of insulin based on the minimization of a risk function. The risk function is based on measurements of a biomarker like glucose, triglycerides, low density lipids, and high density lipids.

However, the development of alternative titrators enabling safe titration is still needed and desirable.

Given the above background, what is needed in the art are systems and methods that provide improved insulin medicament titration in between visits to a health care practitioner.

SUMMARY

The present disclosure addresses the need in the art for systems and methods for providing improved insulin medicament titration in between visits to a health care practitioner. In the present disclosure, a titrator is introduced that has a varying target glucose concentration.

The target glucose concentration in the disclosed titrators is a function of one or more factors affecting glycaemic risk of the subject, such as total blood glucose level variance of the past X days, fasting peripheral glucose level variance of the past X days, minimum blood glucose values of the past X days, rate of change of estimated insulin sensitivity factor, and/or insulin dosage regimen adherence in the past X days, where, here, X is a positive integer. The titrator autonomously adjusts a long acting insulin medicament dosage in response to changes in the target glucose concentration and the actual glucose concentration of the subject.

Accordingly, one aspect of the present disclosure provides a device for autonomously adjusting a long acting insulin medicament dosage in a prescribed insulin regimen for a subject, wherein the device comprises one or more processors and a memory, the memory comprising:

a first data structure that includes the prescribed insulin regimen including a basal insulin medicament dosage regimen, wherein the basal insulin medicament dosage regimen specifies the long acting insulin medicament dosage and wherein the first data structure further comprises (i) a target fasting blood glucose level, (ii) a minimum target fasting blood glucose level and (iii) a maximum target fasting blood glucose level, an indication as to when the subject is to inject and instructions that, when executed by the one or more processors, perform a method of:

obtaining a first data set, the first data set comprising a plurality of glucose measurements of the subject taken over a time course and, for each respective glucose measurement in the plurality of glucose measurements, a corresponding timestamp representing when in the time course the respective glucose measurement was made;

obtaining a second data set (238) from one or more insulin pens used by the subject to apply the prescribed insulin regimen, the second data set comprising a plurality of insulin medicament records over the time course, each insulin medicament record (240) in the plurality of medicament records comprising: (i) a respective insulin medicament injection event (242) representing an insulin medicament injection into the subject using a respective insulin pen in the one or more insulin pens (104) and (ii) a corresponding electronic timestamp (244) that is automatically generated by the respective insulin pen upon occurrence of the respective insulin medicament injection event;

updating a first glycaemic risk measure, wherein the first glycaemic risk measure is:
(i) a total glucose level variability observed across the plurality of glucose measurements,
(ii) a variability in a plurality of fasting glucose levels calculated from the plurality of glucose measurements, or
(iii) a minimum glucose measurement observed in the plurality of glucose measurements;
(iv) a rate of change in an insulin sensitivity factor calculated using the plurality of glucose measurements and the second data set, or
(v) a basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course;

and computing a fasting blood glucose target function that is based upon at least the first glycaemic risk measure thereby obtaining an updated target fasting blood glucose level that is between the minimum target fasting blood glucose level and the maximum target fasting blood glucose level; and adjusting the long acting insulin medicament dosage based upon the updated target fasting blood glucose level.

Hereby is provided a titrator with a variable target fasting blood glucose level, wherein the variation can be based on the input of both glucose and insulin data, and thereby a highly reliable calculation of the target function.

In a further aspect the first glycaemic risk measure is the basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course.

Hereby is provided a titrator with a variable target fasting blood glucose level, wherein the variation can be directly based on the subject adherence to the prescribed regimen.

In a further aspect, the fasting blood glucose target function is based upon at least the first glycaemic risk measure and a second glycaemic risk measure, wherein the first glycaemic risk measure and the second glycaemic risk measure are each independently:
(i) the total glucose level variability observed across the plurality of glucose measurements,
(ii) the variability in the plurality of fasting glucose levels calculated from the plurality of glucose measurements,
(iii) the minimum glucose measurement observed in the plurality of glucose measurements,
(iv) a rate of change in an insulin sensitivity factor calculated using the plurality of glucose measurements and the second data set, or
(v) a basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course.

In a further aspect, a range of possible values for the first glycaemic risk measure and a range of possible values for the second glycaemic risk measure are each dimensions of an N-dimensional space ($\mathbb{R}^N$) and the fasting blood glucose target function has the form:

$$\Sigma_i^{N-1} c_i x_i = FGL$$

wherein,
$c_i$ is an $i^{th}$ constant applied to an $x_i^{th}$ glycaemic risk measure, wherein the $x_i^{th}$ glycaemic risk measure is in a plurality of glycaemic risk measures that includes the first glycaemic risk measure and the second glycaemic risk measure, and wherein i is an integer between one and N−1; and
FGL is the target fasting blood glucose level.

In a further aspect the first glycaemic risk measure is the variability in the plurality of fasting glucose levels,
the second glycaemic risk measure is the basal adherence score over the time course, and,
a range of possible values for the first glycaemic risk measure and a range of possible values for the second glycaemic risk measure are each dimensions of an N-dimensional space ($\mathbb{R}^N$) and the fasting blood glucose target function has the form:

$$c_1 x_1 + c_2 x_2 = FGL$$

wherein,
$c_1$ is a constant applied to the first glycaemic risk measure,
$c_2$ is a constant applied to the second glycaemic risk measure, and
FGL is the target fasting blood glucose level.

In a further aspect, the first glycaemic risk measure is the variability in the plurality of fasting glucose levels,
the second glycaemic risk measure is the basal adherence score over the time course, and,
a third glycaemic risk measure is the minimum glucose measurement in the plurality of glucose measurements of the subject, and
the fasting blood glucose target function is a function of:
(i) the variability in the plurality of fasting glucose levels as a first dimension of the N-dimensional space,
(ii) the basal adherence score over the time course as a second dimension of the N-dimensional space, and (iii) and the minimum glucose measurement in the plurality of glucose measurements of the subject as a third dimension of the N-dimensional space.

In a further aspect, a range of possible values for the variability in the plurality of fasting glucose levels define a first dimension a three-dimensional space ($\mathbb{R}^3$), a range of possible values for the basal adherence score over the time course define a second dimension in the three-dimensional space, and a range of possible values for the minimum glucose measurement define a third-dimension in the three dimensional space, and the fasting blood glucose target function has the form:

$$c_1 x + c_2 y + c_3 z = FGL$$

wherein,
$c_1$ is a first constant applied to the variability in the plurality of fasting glucose levels,
$c_2$ is a second constant applied to the basal adherence score over the time course,
$c_3$ is a third constant applied to the minimum glucose measurement, and
FGL is the target fasting blood glucose level.

In a further aspect, the method further comprises:
storing the updated target fasting blood glucose level in the first data structure and wherein
the method is repeated on a recurring basis.

In a further aspect, the successive measurements in the plurality of glucose measurements are autonomously taken from the subject at an interval rate of 5 minutes or less, 3 minutes or less, or 1 minute or less.

In a further aspect, the device further comprises a wireless receiver (284), and wherein the first data set is obtained wirelessly from a glucose sensor (102) affixed to the subject and/or the second data set is obtained wirelessly from the one or more insulin pens (104).

In a further aspect, the first glycaemic risk measure or the second glycaemic risk measure is the total glucose level variability observed across the plurality of glucose measurements computed as one of (i), (ii), (iii), or (iv):
(i) a range of total glucose levels in the plurality of glucose levels,
(ii) an interquartile range of glucose levels in the plurality of glucose levels,
(iii) an average squared difference of the glucose levels in the plurality of glucose levels from the mean (μ) of the plurality of glucose levels ($\sigma^2$) computed as:

$$\sigma^2 = \frac{\sum_i^P (m_i - \mu)^2}{P}$$

wherein,
$m_i$ is the $i^{th}$ glucose levels in the plurality of glucose levels, and
P is the number of glucose levels in the plurality of glucose levels, and
(iv) the standard deviation of the glucose levels in the plurality of glucose levels computed as $\sqrt{\sigma^4}$.

In a further aspect, the first glycaemic risk measure or the second glycaemic risk measure is the variability in the plurality of fasting glucose levels calculated from the plurality of glucose measurements computed as one of (i), (ii), (iii), or (iv):
(i) a range of fasting glucose levels in the plurality of fasting glucose levels,
(ii) an interquartile range of fasting glucose levels in the plurality of fasting glucose levels,
(iii) an average squared difference of the fasting glucose levels in the plurality of fasting glucose levels from the mean (μ) of the plurality of fasting glucose levels ($\sigma^2$) computed as:

$$\sigma^2 = \frac{\sum_i^P (m_i - \mu)^2}{P}$$

wherein,
$m_i$ is the $i^{th}$ fasting glucose levels in the plurality of fasting glucose levels, and
P is the number of fasting glucose levels in the plurality of fasting glucose levels, and
(iv) the standard deviation of the fasting glucose levels in the plurality of fasting glucose levels computed as $\sqrt{\sigma^2}$.

In a further aspect, the method further comprises:

autonomously obtaining a third data set, the third data set comprising one or more physiological measurements of the subject; and the fasting blood glucose target function is based upon at least the first glycaemic risk measure and a second glycaemic risk measure, wherein the first glycaemic risk measure and the second glycaemic risk measure are each independently:

(i) the total glucose level variability observed across the plurality of glucose measurements, (ii) the variability in the plurality of fasting glucose levels calculated from the plurality of glucose measurements, (iii) the minimum glucose measurement observed in the plurality of glucose measurements, or (iv) the one or more physiological measurements of the subject.

In a further aspect, the method further comprises:

autonomously obtaining a third data set, the third data set comprising one or more physiological measurements of the subject; and the fasting blood glucose target function is based upon at least the first glycaemic risk measure, the second glycaemic risk measure and a third glycaemic risk measure, wherein the first glycaemic risk measure, the second glycaemic risk measure, and the third glycaemic risk measure are each independently:

(i) the total glucose level variability observed across the plurality of glucose measurements, (ii) the variability in the plurality of fasting glucose levels calculated from the plurality of glucose measurements, (iii) the minimum glucose measurement observed in the plurality of glucose measurements, (iv) the rate of change in an insulin sensitivity factor calculated using the plurality of glucose measurements and the second data set, (v) the basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course; or (vi) the one or more physiological measurements of the subject.

In a further aspect, each physiological measurement in the one or more physiological measurements is a body temperature of the subject or a measurement of cardiovascular activity of the subject.

In a further aspect is provided a method for autonomously adjusting a long acting insulin medicament dosage in a prescribed insulin regimen for a subject, the method comprising:

obtaining a first data set (228), the first data set comprising a plurality of glucose measurements of the subject taken over a time course and, for each respective glucose measurement (230) in the plurality of glucose measurements, a corresponding timestamp (232) representing when in the time course the respective glucose measurement was made;

obtaining a second data set (238) from one or more insulin pens used by the subject to apply the prescribed insulin regimen, the second data set comprising a plurality of insulin medicament records over the time course, each insulin medicament record (240) in the plurality of medicament records comprising: (i) a respective insulin medicament injection event (242) representing an insulin medicament injection into the subject using a respective insulin pen in the one or more insulin pens (104) and (ii) a corresponding electronic timestamp (244) that is automatically generated by the respective insulin pen upon occurrence of the respective insulin medicament injection event;

updating a first glycaemic risk measure (236), wherein the first glycaemic risk measure is:

(i) a total glucose level variability observed across the plurality of glucose measurements, (ii) a variability in a plurality of fasting glucose levels calculated from the plurality of glucose measurements, or (iii) a minimum glucose measurement observed in the plurality of glucose measurements;

(iv) a rate of change in an insulin sensitivity factor calculated using the plurality of glucose measurements and the second data set, or (v) a basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course;

and computing a fasting blood glucose target function that is based upon at least the first glycaemic risk measure thereby obtaining an updated target fasting blood glucose level that is between the minimum target fasting blood glucose level (226) and the maximum target fasting blood glucose level (227); and adjusting the long acting insulin medicament dosage based upon the updated target fasting blood glucose level.

In another aspect of the present disclosure, a computer program is provided comprising instructions that, when executed by one or more processors, perform a method comprising:

obtaining a first data set (228), the first data set comprising a plurality of glucose measurements of the subject taken over a time course and, for each respective glucose measurement (230) in the plurality of glucose measurements, a corresponding timestamp (232) representing when in the time course the respective glucose measurement was made;

obtaining a second data set (238) from one or more insulin pens used by the subject to apply the prescribed insulin regimen, the second data set comprising a plurality of insulin medicament records over the time course, each insulin medicament record (240) in the plurality of medicament records comprising: (i) a respective insulin medicament injection event (242) representing an insulin medicament injection into the subject using a respective insulin pen in the one or more insulin pens (104) and (ii) a corresponding electronic timestamp (244) that is automatically generated by the respective insulin pen upon occurrence of the respective insulin medicament injection event;

updating a first glycaemic risk measure (236), wherein the first glycaemic risk measure is:
(i) a total glucose level variability observed across the plurality of glucose measurements,
(ii) a variability in a plurality of fasting glucose levels calculated from the plurality of glucose measurements, or
(iii) a minimum glucose measurement observed in the plurality of glucose measurements;
(iv) a rate of change in an insulin sensitivity factor calculated using the plurality of glucose measurements and the second data set, or
(v) a basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course;
and
computing a fasting blood glucose target function that is based upon at least the first glycaemic risk measure thereby obtaining an updated target fasting blood glucose level that is between the minimum target fasting blood glucose level (226) and the maximum target fasting blood glucose level (227); and
adjusting the long acting insulin medicament dosage based upon the updated target fasting blood glucose level.

In a further aspect is provided a computer-readable data carrier having stored thereon the computer program.

In another aspect the present disclosure provides a device for autonomously adjusting a long acting insulin medicament dosage in a prescribed insulin regimen for a subject. The device comprises one or more processors and a memory. The memory comprises a first data structure, which includes the prescribed insulin regimen including a basal insulin medicament dosage regimen, and instructions. The basal insulin medicament dosage regimen specifies a long acting insulin medicament dosage. The first data structure further comprises an original target fasting blood glucose level used as a basis to compute the long acting insulin medicament dosage as well as minimum and maximum target fasting blood glucose levels. The instructions, when executed by the one or more processors, perform a method.

In the method a first data set is obtained. The first data set comprises a plurality of glucose measurements of the subject taken over a time course. For each respective glucose measurement in the plurality of glucose measurements, there is a timestamp representing when in the time course the respective glucose measurement was made.

A first glycaemic risk measure is updated.

In some embodiments, the first glycaemic risk measure is: (i) a total glucose level variability observed across the plurality of glucose measurements, (ii) variability in a plurality of fasting glucose levels calculated from the plurality of glucose measurements, or (iii) a minimum glucose measurement observed in the plurality of glucose measurements.

In some embodiments, the first glycaemic risk measure is:
(i) a total glucose level variability observed across the plurality of glucose measurements,
(ii) a variability in the plurality of fasting glucose levels calculated from the plurality of glucose measurements,
(iii) a minimum glucose measurement observed in the plurality of glucose measurements,
(iv) a rate of change in an insulin sensitivity factor calculated using the plurality of glucose measurements and the second data set,
(v) a basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course,
(vi) one or more physiological measurements of the subject, or
a function of any one of (i) through (vi).

The method continues with the computing of a fasting blood glucose target function that is based upon the first glycaemic risk measure thereby obtaining an updated target fasting blood glucose level that is between a minimum target fasting blood glucose level (226) and a maximum target fasting blood glucose level (227). The long acting insulin medicament dosage is then adjusted based upon the new target fasting blood glucose level.

In some embodiments, the first data structure further comprises an indication as to when the subject is to inject the long acting insulin medicament dosage. In such embodiments, the method further comprises obtaining a second data set (238) from one or more insulin pens used by the subject to apply the prescribed insulin regimen. The second data set comprises a plurality of insulin medicament records over the time course. Each insulin medicament record in the plurality of medicament records comprises: (i) a respective insulin medicament injection event representing an insulin medicament injection into the subject using a respective insulin pen in the one or more insulin pens and (ii) a corresponding electronic timestamp that is automatically generated by the respective insulin pen upon occurrence of the respective insulin medicament injection event. Further, in such embodiments, the fasting blood glucose target function is based upon at least the first glycaemic risk measure and a second glycaemic risk measure, where the first glycaemic risk measure and the second glycaemic risk measure are each independently: (i) a total glucose level variability observed across the plurality of glucose measurements, (ii) a variability in the plurality of fasting glucose levels calculated from the plurality of glucose measurements, (iii) a minimum glucose measurement observed in the plurality of glucose measurements, (iv) a rate of change in an insulin sensitivity factor calculated using the plurality of glucose measurements and the second data set, or (v) a basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course.

In some embodiments, a range of possible values for the first glycaemic risk measure and a range of possible values for the second glycaemic risk measure are each dimensions of an N-dimensional space ($\mathbb{R}^N$) (e.g., $\mathbb{R}^3$ if the fasting blood glucose target function is limited to the first and second glycaemic risk measures, where the third dimension is the target fasting blood glucose level, but some higher dimension if the fasting blood glucose target function includes more than the first and second glycaemic risk measures). Further, the fasting blood glucose target function has the form $\Sigma_i^{N-1} c_i x_i = FGL$ where, $c_i$ is an $i^{th}$ constant applied to an $x_i^{th}$ glycaemic risk measure, and the $x_i^{th}$ glycaemic risk measure is in a plurality of glycaemic risk measures that includes the first glycaemic risk measure and the second glycaemic risk measure. Further, i is an integer between one and N−1 and FGL is the target fasting blood glucose level. However, in some embodiments FGL is expressed as a nonlinear function of the glycaemic risk measures. In some embodiments, the fasting blood glucose target function has the form $f(\{x_1, \ldots, x_{N-1}\})=$FGL where, f is a linear or nonlinear function of the plurality of glycaemic risk measures $\{x_1, \ldots, x_{N-1}\}$. An example of a fasting blood glucose target function of form $f(\{x_1, \ldots, x_{N-1}\})$ is $\Sigma_i^{N-1} c_i x_i$ which calls for a weighted summation of the glycaemic risk measures.

In some embodiments, a range of possible values for the first glycaemic risk measure and a range of possible values for the second glycaemic risk measure are each dimensions of an N-dimensional space ($\mathbb{R}^N$) (e.g., $\mathbb{R}^3$ if the fasting blood glucose target function is limited to the first and second glycaemic risk measures, where the third dimension is the target fasting blood glucose level, but some higher dimension if the fasting blood glucose target function includes more than the first and second glycaemic risk measures). Further, the fasting blood glucose target function has the form $\Sigma_i^{N-1} f_i(x_i)=$FGL where, $f_i$ is an $i^{th}$ function of an $x_i^{th}$ glycaemic risk measure, and the $x_i^{th}$ glycaemic risk measure is in a plurality of glycaemic risk measures that includes the first glycaemic risk measure and the second glycaemic risk measure. Further, i is an integer between one and N−1 and FGL is the target fasting blood glucose level, which in this embodiment is a composite of the functions $f_i$. Examples of fasting blood glucose target function of the form $f_i(x_i)$ include, but are not limited to, functions that raise $x_i$ to a power, functions that take an inverse of $x_i$, functions that negate $x_i$, to name a few nonlimiting possibilities.

In some embodiments, a range of possible values for the first glycaemic risk measure, a range of possible values for the second glycaemic risk, and a range of values for the target fasting blood glucose level define a three dimensional space ($\mathbb{R}^3$) and the fasting blood glucose target function has the form $c_1 x + c_2 y =$FGL. Here, $c_1$ is a first constant applied to the first glycaemic risk measure, $c_2$ is a second constant applied to the second glycaemic risk measure, and FGL is the fasting glucose level.

In some embodiments, the first glycaemic risk measure is the variability in the plurality of fasting glucose levels, the second glycaemic risk measure is the basal adherence score over the time course, and a third glycaemic risk measure is the minimum glucose measurement in the plurality of glucose measurements of the subject. In such embodiments, the fasting blood glucose target function comprises (i) a variability in the plurality of fasting glucose levels as a first dimension of the N-dimensional space, (ii) a basal adherence score over the time course as a second dimension of the N-dimensional space, and (iii) and a minimum glucose measurement in the plurality of glucose measurements of the subject as a third dimension of the N-dimensional space.

In some embodiments, a range of possible values for the variability in the plurality of fasting glucose levels, a range of possible values for the basal adherence score over the time course, and a range of possible values for the minimum glucose measurement define a four-dimensional space ($\mathbb{R}^4$) and the fasting blood glucose target function has the form $c_1 x + c_2 y + c_3 z =$FGL, where $c_1$ is a first constant applied to the variability in the plurality of fasting glucose levels, $c_2$ is a second constant applied to the basal adherence score over the time course, $c_3$ is a third constant applied to the minimum glucose measurement, and FGL is the calculated target fasting blood glucose level.

In some embodiments, the method further comprises storing the calculated target fasting blood glucose level in the first data structure and the method is repeated on a recurring basis.

In some embodiments, successive measurements in the plurality of glucose measurements are autonomously taken from the subject at an interval rate of 5 minutes or less, 3 minutes or less, or 1 minute or less.

In some embodiments, the device used to carry out the method further comprises a wireless receiver and the first data set is obtained wirelessly from a glucose sensor affixed to the subject and/or the second data set is obtained wirelessly from the one or more insulin pens.

In some embodiments, the first glycaemic risk measure or the second glycaemic risk measure is the total glucose level variability observed across the plurality of glucose measurements computed as one of (i), (ii), (iii), or (iv): (i) a range of total glucose levels in the plurality of glucose levels, (ii) an interquartile range of glucose levels in the plurality of glucose levels, (iii) an average squared difference of the glucose levels in the plurality of glucose levels from the mean ($\mu$) of the plurality of glucose levels ($\sigma^2$) computed as $$\sigma^2 = \frac{\sum_i^P (m_i - \mu)^2}{P},$$

where $m_i$ is the $i^{th}$ glucose levels in the plurality of glucose levels, and P is the number of glucose levels in the plurality of glucose levels, and (iv) the standard deviation of the glucose levels in the plurality of glucose levels computed as $\sqrt{\sigma^2}$.

In some embodiments, the first glycaemic risk measure or the second glycaemic risk measure is the variability in the plurality of fasting glucose levels calculated from the plurality of glucose measurements computed as one of (i), (ii), (iii), or (iv): (i) a range of fasting glucose levels in the plurality of fasting glucose levels, (ii) an interquartile range of fasting glucose levels in the plurality of fasting glucose levels, (iii) an average squared difference of the fasting glucose levels in the plurality of fasting glucose levels from the mean ($\mu$) of the plurality of fasting glucose levels ($\sigma^2$) computed as, $$\sigma^2 = \frac{\sum_i^P (m_i - \mu)^2}{P}$$

where, $m_i$ is the $i^{th}$ fasting glucose levels in the plurality of fasting glucose levels, and P is the number of fasting glucose levels in the plurality of fasting glucose levels, and (iv) the standard deviation of the fasting glucose levels in the plurality of fasting glucose levels computed as $\sqrt{\sigma^2}$.

In some embodiments, the method further comprises autonomously obtaining one or more physiological measurements of the subject. In such embodiments, the fasting blood glucose target function is based upon at least a first glycaemic risk measure and a second glycaemic risk measure, where the first glycaemic risk measure and the second glycaemic risk measure are each independently: (i) a total glucose level variability observed across the plurality of glucose measurements, (ii) a variability in the plurality of fasting glucose levels calculated from the plurality of glucose measurements, (iii) a minimum glucose measurement observed in the plurality of glucose measurements, or (iv) the one or more physiological measurements of the subject. In some such embodiments each physiological measurement in the one or more physiological measurements is a body temperature of the subject or a measurement of cardiovascular activity of the subject.

In some embodiments, the method further comprises autonomously obtaining a third data set, the third data set comprising one or more physiological measurements of the subject.

In such embodiments, the fasting blood glucose target function is based upon at least the first glycaemic risk measure, the second glycaemic risk measure and a third glycaemic risk measure, where the first glycaemic risk measure, the second glycaemic risk measure, and the third glycaemic risk measure are each independently: (i) a total glucose level variability observed across the plurality of glucose measurements, (ii) a variability in the plurality of fasting glucose levels calculated from the plurality of glucose measurements, (iii) a minimum glucose measurement observed in the plurality of glucose measurements, (iv) a rate of change in an insulin sensitivity factor calculated using the plurality of glucose measurements and the second data set, (v) a basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course, or (vi) the one or more physiological measurements of the subject. In some such embodiments each physiological measurement in the one or more physiological measurements is a body temperature of the subject or a measurement of cardiovascular activity of the subject.

BRIEF DESCRIPTION OF THE DRAWINGS

FIGS. 4A, 4B, 4C, 4D, and 4E collectively provide a flow chart of processes and features of a device for autonomously adjusting a long acting insulin medicament dosage in a prescribed insulin regimen in accordance with various embodiments of the present disclosure.

Like reference numerals refer to corresponding parts throughout the several views of the drawings.

DETAILED DESCRIPTION

Figure 1:
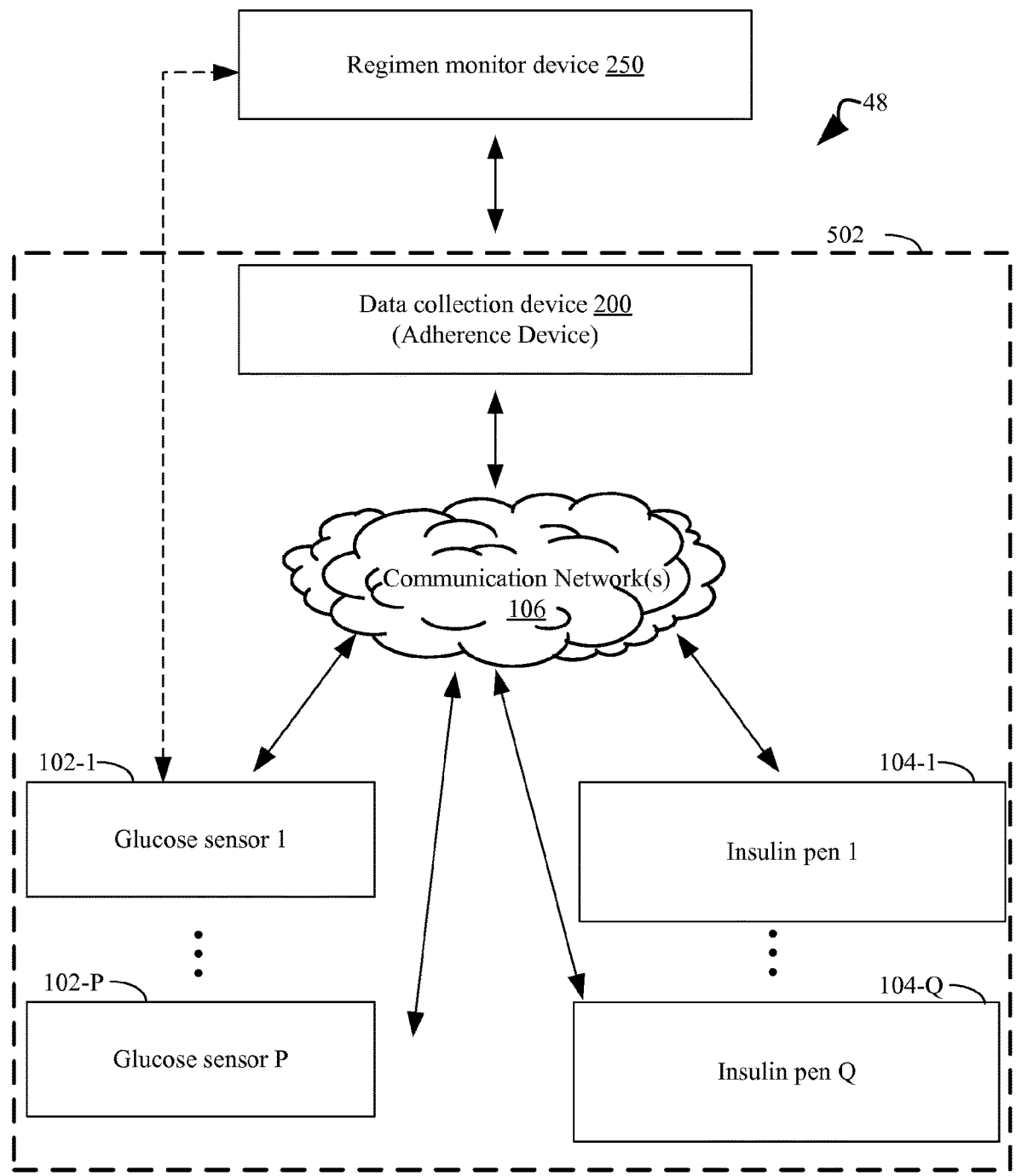
FIG. 1 illustrates an exemplary system topology that includes a regimen monitor device for autonomously adjusting a long acting insulin medicament dosage in a prescribed insulin regimen for a subject, a data collection device for collecting patient data, one or more glucose sensors that measure glucose data from the subject, and one or more insulin pens that are used by the subject to inject insulin medicaments in accordance with the prescribed insulin medicament regimen, where the above-identified components are interconnected, optionally through a communications network, in accordance with an embodiment of the present disclosure.
Figure 5:
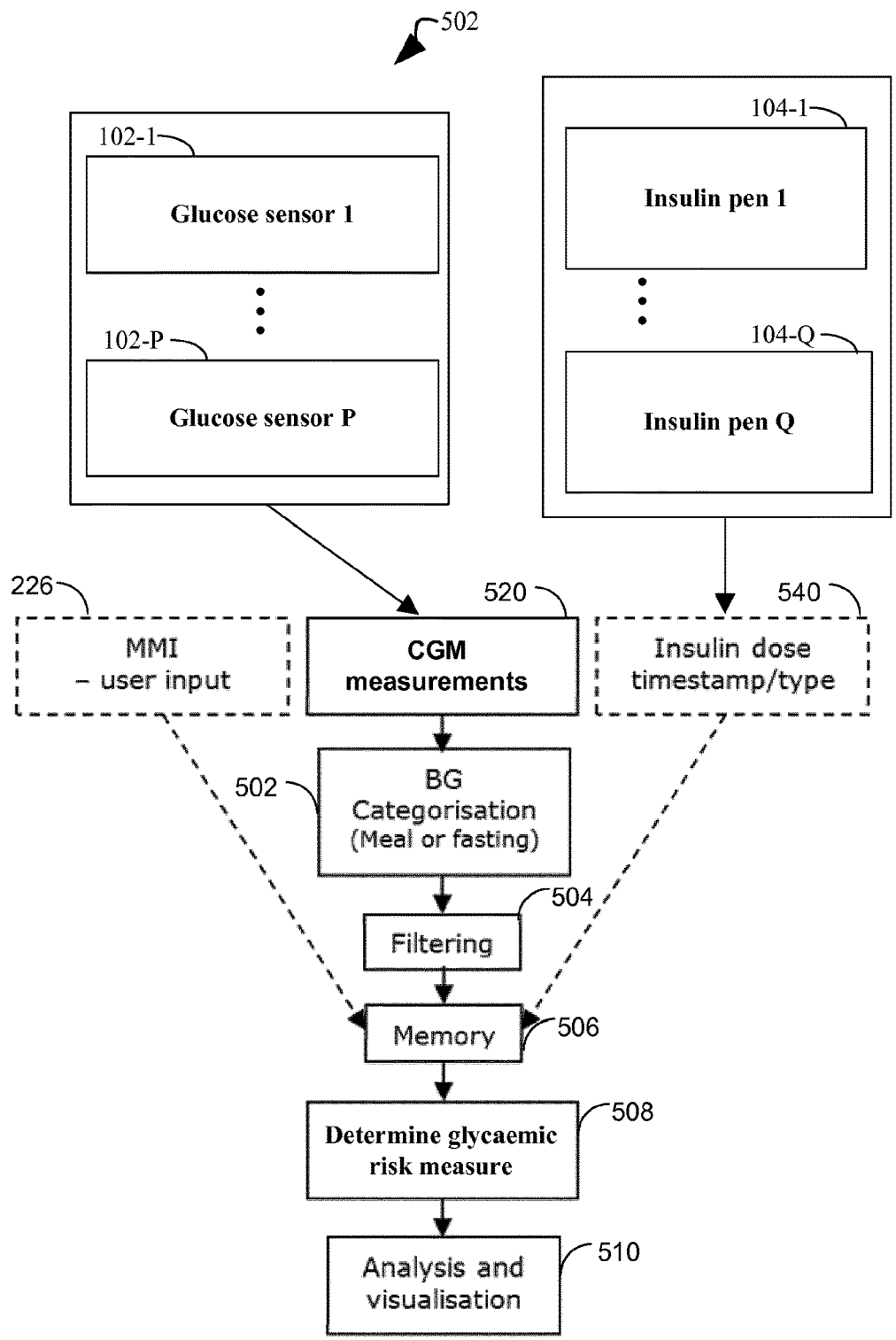
FIG. 5 illustrates an example integrated system of connected insulin pen(s), continuous glucose monitor(s), memory and a processor for autonomously adjusting a long acting insulin medicament dosage in a prescribed insulin regimen in accordance with an embodiment of the present disclosure.
Figure 6:
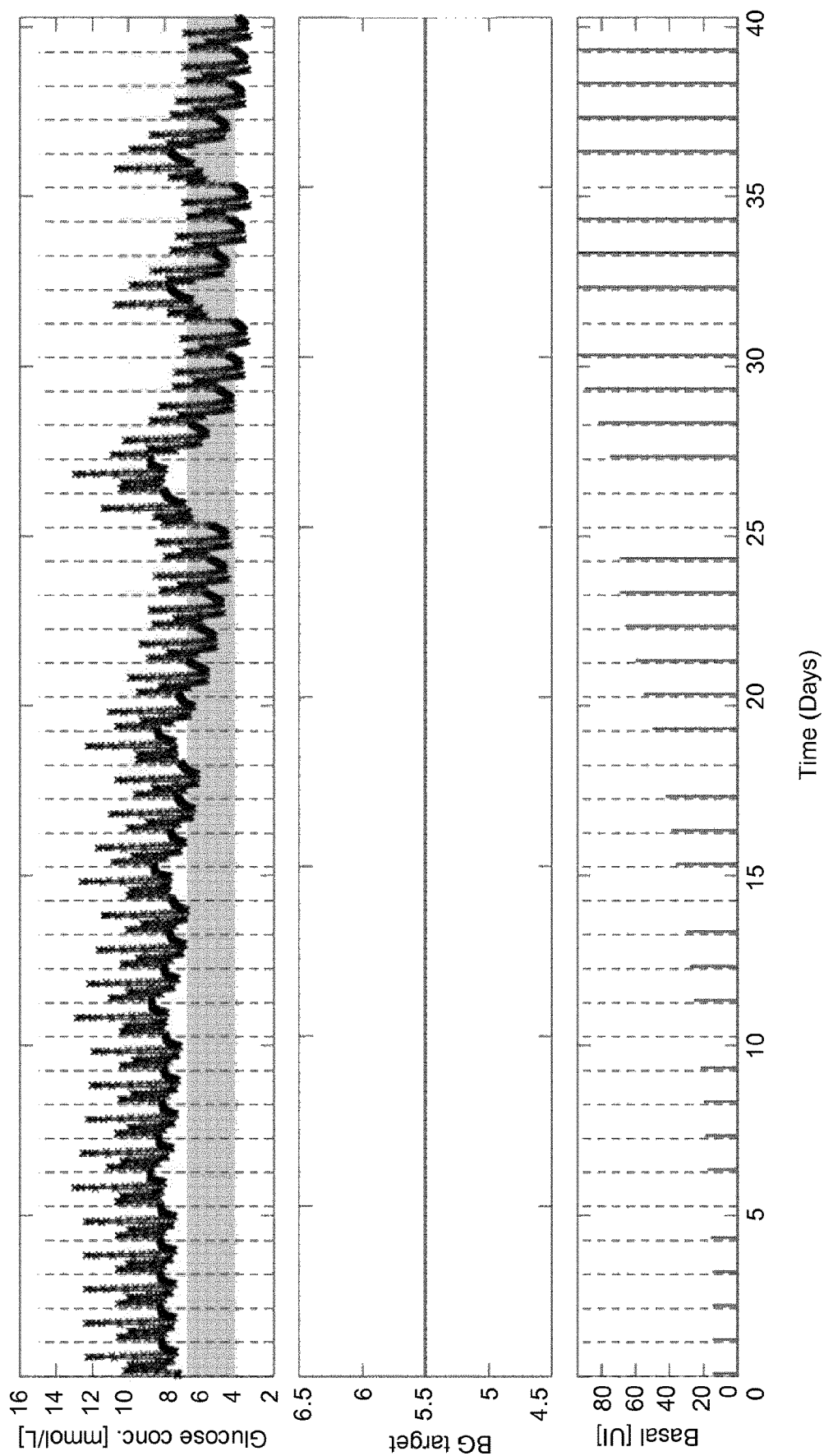
FIG. 6 illustrates an example simulation of a titrator, with a constant glucose target, for titrating a type 2 diabetic patient over 40 days, in accordance with the prior art. The top panel shows blood glucose concentration during basal titration over the 40 days. Every few days the patient forgets to take his basal. The basal titration algorithm is similar to the one defined in U.S. Pat. No. 8,370,077 B2, with a constant target, and leads to hypoglycaemic events in the simulation.
Figure 7:
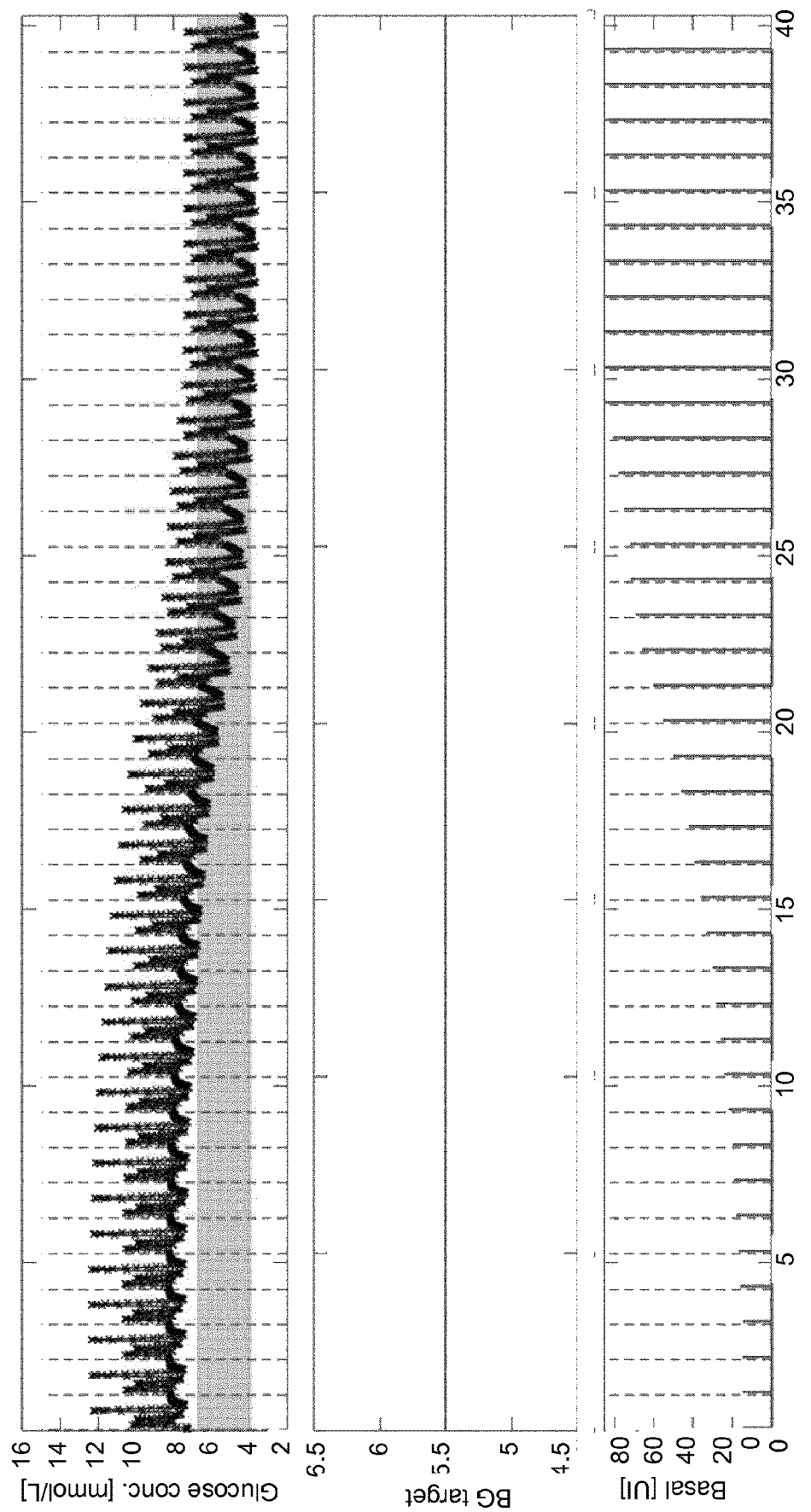
FIG. 7 illustrates an example simulation of a titrator, with a constant glucose target, for titrating a type 2 diabetic patient over 40 days, in accordance with the prior art. The top panel shows blood glucose concentration during basal titration over the 40 days. Every few days the fasting glucose measurement is too high due to some unknown reason. The basal titration algorithm is similar to the one defined in U.S. Pat. No. 8,370,077 B2, with a constant target, and leads to hypoglycaemic events in the simulation.

The present disclosure relies upon the acquisition of data regarding a data set comprising a plurality of glucose measurements of a subject taken over a time course and, for each respective glucose measurement in the plurality of glucose measurements, a corresponding timestamp representing when in the time course the respective glucose measurement was made. FIG. 1 illustrates an example of an integrated system 502 for the acquisition of such data, and FIG. 5 provides more details of such a system 502. The integrated system 502 includes one or more connected insulin pens 104, one or more glucose monitors 102, memory 506, and a processor (not shown) for performing algorithmic categorization of autonomous glucose data of a subject. In some embodiments, a glucose monitor 102 is a continuous glucose monitor.

With the integrated system 502, autonomous timestamped glucose measurements of the subject are obtained 520. Also, in some embodiments, data from the one or more insulin pens 104 used to apply a prescribed insulin regimen to the subject is obtained 540 as a plurality of records. Each record comprises a timestamped event specifying an amount of injected insulin medicament that the subject received as part of the prescribed insulin medicament dosage regimen. The glucose measurements are filtered 504 and stored in non-transitory memory 506. The plurality of glucose measurements of the subject taken over a time are used to determine the glycaemic risk of the subject 508. In this way, the glucose data is analyzed and visualized (e.g., to adjust the long acting insulin medicament dosage based upon an updated target fasting blood glucose level) in accordance with the methods of the present disclosure 510.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject" and "user" are used interchangeably herein. By the term insulin pen is meant an injection device suitable for applying discrete doses of insulin, and wherein the injection device is adapted for logging and communicating dose related data.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 2:
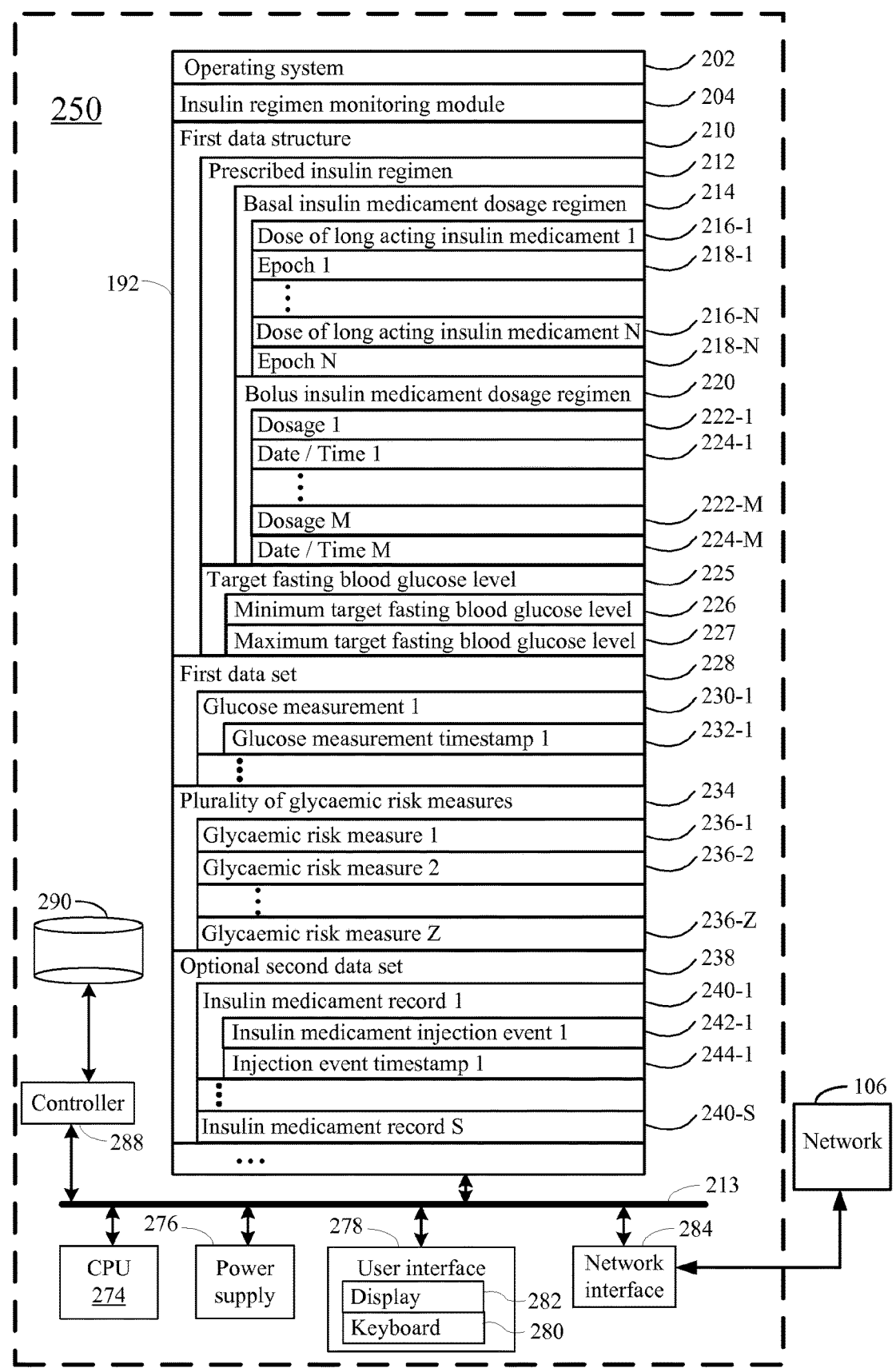
FIG. 2 illustrates a device for autonomously adjusting a long acting insulin medicament dosage in a prescribed insulin regimen in accordance with an embodiment of the present disclosure.
Figure 3:
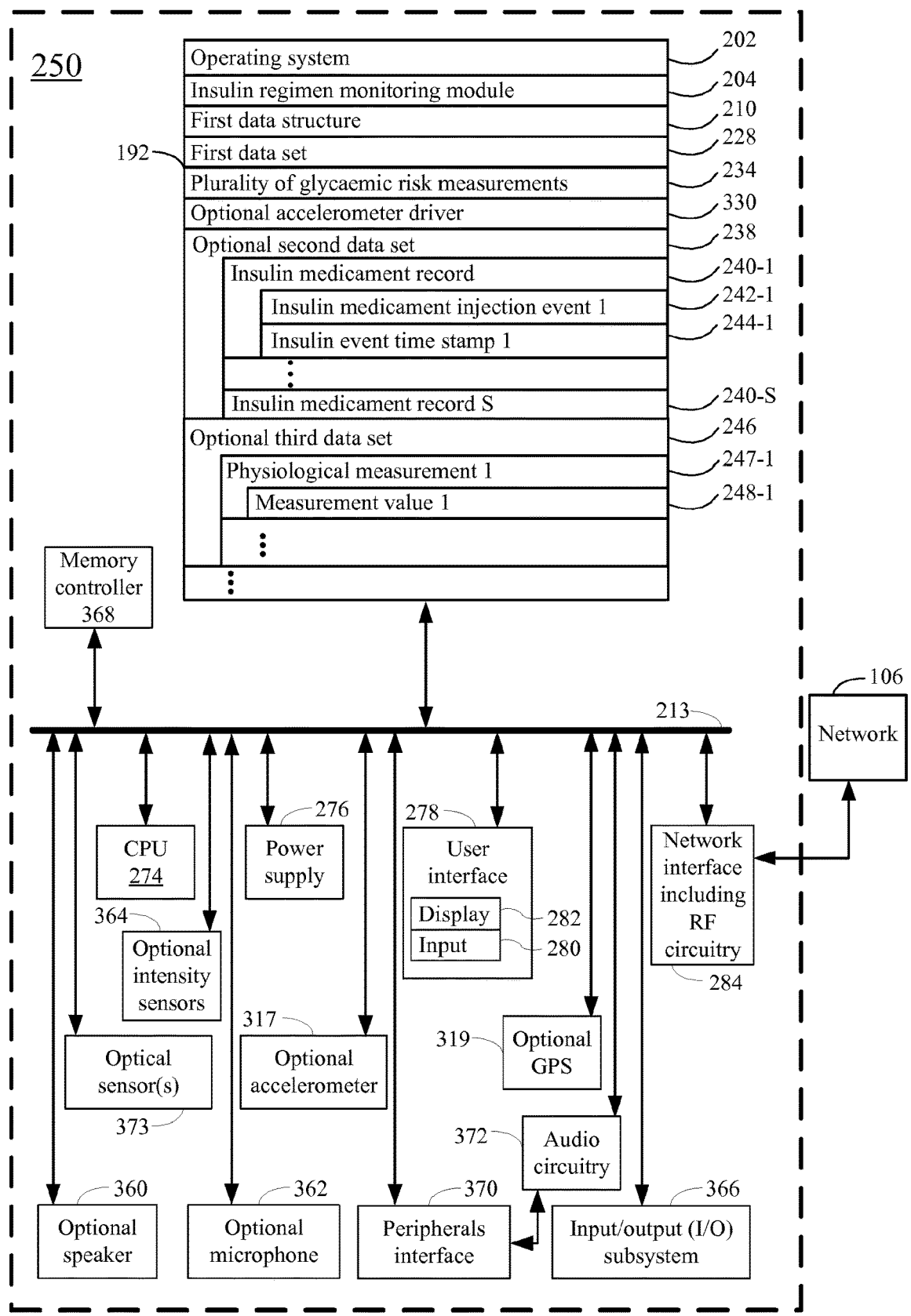
FIG. 3 illustrates a device for autonomously adjusting a long acting insulin medicament dosage in a prescribed insulin regimen in accordance with another embodiment of the present disclosure.

A detailed description of a system 48 for autonomously adjusting a long acting insulin medicament dosage in a prescribed insulin regimen for a subject in accordance with the present disclosure is described in conjunction with FIGS. 1 through 3. As such, FIGS. 1 through 3 collectively illustrate the topology of the system in accordance with the present disclosure. In the topology, there is a regimen monitoring device for autonomously adjusting a long acting insulin medicament dosage in a prescribed insulin regimen for a subject ("regimen monitor device 250") (FIGS. 1, 2, and 3), a device for data collection ("data collection device 200"), one or more glucose sensors 102 associated with the subject (FIGS. 1 and 5), and one or more insulin pens 104 for injecting insulin medicaments into the subject (FIGS. 1 and 5). Throughout the present disclosure, the data collection device 200 and the regimen monitor device 250 will be referenced as separate devices solely for purposes of clarity. That is, the disclosed functionality of the data collection device 200 and the disclosed functionality of the regimen monitor device 250 are contained in separate devices as illustrated in FIG. 1. However, it will be appreciated that, in fact, in some embodiments, the disclosed functionality of the data collection device 200 and the disclosed functionality of the regimen monitor device 250 are contained in a single device. In some embodiments, the disclosed functionality of the data collection device 200 and/or the disclosed functionality of the regimen monitor device 250 are contained in a single device and this single device is a glucose monitor 102 or the insulin pen 104.

Referring to FIG. 1, the regimen monitor device 250 autonomously adjusts a long acting insulin medicament dosage in a prescribed insulin regimen for a subject. To do this, the data collection device 200, which is in electrical communication with the regimen monitor device 250, receives autonomous glucose measurements originating from one or more glucose sensors 102 attached to a subject on an ongoing basis. In some embodiments, the data collection device 200 also receives insulin medicament injection data from one or more insulin pens 104 used by the subject to inject insulin medicaments. In some embodiments, the data collection device 200 receives such data directly from the glucose sensor(s) 102 and insulin pens 104 used by the subject. For instance, in some embodiments the data collection device 200 receives this data wirelessly through radio-frequency signals. In some embodiments such signals are in accordance with an 802.11 (WiFi), Bluetooth, or ZigBee standard. In some embodiments, the data collection device 200 receives such data directly, analyzes the data, and passes the analyzed data to the regimen monitor device 250. In some embodiments, a glucose sensor 102 and/or insulin pen 104 includes an RFID tag and communicates to the data collection device 200 and/or the regimen monitor device 250 using RFID communication. In some embodiments, the data collection device 200 also obtains or receives physiological measurements 247 of the subject (e.g., from wearable physiological measurement devices, from measurement devices within the data collection device 200 such as a magnetometer or thermostat, etc).

In some embodiments, the data collection device 200 and/or the regimen monitor device 250 is not proximate to the subject and/or does not have wireless capabilities or such wireless capabilities are not used for the purpose of acquiring glucose data, insulin medicament injection data, and/or physiological measurement data. In such embodiments, a communication network 106 may be used to communicate glucose measurements from the glucose sensor 102 to the data collection device 200 and/or the regimen monitor device 250, insulin medicament injection data from the one or more insulin pens 104 to the data collection device 200 and/or the regimen monitor device 250, and/or physiological measurement data from one or more physiological measurement devices (not shown) to the data collection device 200 and/or the regimen monitor device 250.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

In some embodiments, there is a single glucose sensor 102 attached to the subject and the data collection device 200 and/or the regimen monitor device 250 is part of the glucose sensor 102. That is, in some embodiments, the data collection device 200 and/or the regimen monitor device 250 and the glucose sensor 102 are a single device.

In some embodiments, the data collection device 200 and/or the regimen monitor device 250 is part of an insulin pen. That is, in some embodiments, the data collection device 200 and/or the regimen monitor device 250 and an insulin pen 104 are a single device.

Of course, other topologies of the system 48 are possible. For instance, rather than relying on a communications network 106, the one or more glucose sensors 102 and the one or more insulin pens 104 may wirelessly transmit information directly to the data collection device 200 and/or regimen monitor device 250. Further, the data collection device 200 and/or the regimen monitor device 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the regimen monitor device 250 comprises one or more computers. For purposes of illustration in FIG. 2, the regimen monitor device 250 is represented as a single computer that includes all of the functionality for evaluating historical adherence to a prescribed insulin medicament dosage regimen for a subject. However, the disclosure is not so limited. In some embodiments, the functionality for autonomously adjusting a long acting insulin medicament dosage in a prescribed insulin regimen for a subject is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary regimen monitor device 250 for autonomously adjusting a long acting insulin medicament dosage in a prescribed insulin regimen for a subject comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the regimen monitor device 250 but that can be electronically accessed by the regimen monitor device 250 over an Internet, intranet, or other form of network or electronic cable (illustrated as element 106 in FIG. 2) using network interface 284.

In some embodiments, the memory 192 of the regimen monitor device 250 for autonomously adjusting a long acting insulin medicament dosage in a prescribed insulin regimen for a subject stores:
- an operating system 202 that includes procedures for handling various basic system services;
- an insulin regimen monitoring module 204;
- a first data structure 210, the first data structure comprising a prescribed insulin regimen 212 for the subject, a target fasting blood glucose level 225, a minimum target fasting blood glucose level 226, and a maximum target fasting blood glucose level 227, and furthermore the prescribed insulin regimen comprises a basal insulin medicament dosage regimen 214 and, optionally in some embodiments, a bolus insulin medicament dosage regimen 220;
- a first data set 220, the first data set representing a time course and comprising a plurality of glucose measurements of the subject over the time course, and for each respective glucose measurement 230 in the plurality of glucose measurements, a timestamp 232 representing when the respective glucose measurement was made;
- a plurality of glycaemic risk measures 234 for the subject, each respective glycaemic risk measure 236 in the plurality of glycaemic risk measures independently representing a glycaemic risk to the subject; and an optional second data set 238 comprising a plurality of insulin medicament records, where each respective insulin medicament record 240 in the plurality of insulin medicament records comprises a respective insulin medicament injection event 242 associated with the one or more insulin pens 104 in which an insulin medicament was injected into the subject and an injection event time stamp 244 that indicates when the respective medicament injection event 242 occurred.

In some embodiments, the insulin regimen monitoring module 204 is accessible within any browser (phone, tablet, laptop/desktop). In some embodiments the insulin regimen monitoring module 204 runs on native device frameworks, and is available for download onto the regimen monitor device 250 running an operating system 202 such as Android or iOS.

In some implementations, one or more of the above identified data elements or modules of the regimen monitor device 250 for autonomously adjusting a long acting insulin medicament dosage in a prescribed insulin regimen for a subject are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a regimen monitor device 250 for autonomously adjusting a long acting insulin medicament dosage 216 in a prescribed insulin regimen 212 for a subject is a smart phone (e.g., an iPHONE), laptop, tablet computer, desktop computer, or other form of electronic device (e.g., a gaming console). In some embodiments, the regimen monitor device 250 is not mobile. In some embodiments, the regimen monitor device 250 is mobile.

FIG. 3 provides a further description of a specific embodiment of a regimen monitor device 250 that can be used with the instant disclosure. The regimen monitor device 250 illustrated in FIG. 3 has one or more processing units (CPU's) 274, peripherals interface 370, memory controller 368, a network or other communications interface 284, a memory 192 (e.g., random access memory), a user interface 278, the user interface 278 including a display 282 and input 280 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the regimen monitor device 250 (e.g., a touch-sensitive surface such as a touch-sensitive display system 282 of the regimen monitor device 250), an optional input/output (I/O) subsystem 366, one or more optional optical sensors 373, one or more communication busses 213 for interconnecting the aforementioned components, and a power supply 276 for powering the aforementioned components.

In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons.

The regimen monitor device 250 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the regimen monitor device 250 and/or for determining an amount of physical exertion by the subject.

It should be appreciated that the regimen monitor device 250 illustrated in FIG. 3 is only one example of a multi-function device that may be used for autonomously adjusting a long acting insulin medicament dosage (216) in a prescribed insulin regimen for a subject, and that the regimen monitor device 250 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 192 of the regimen monitor device 250 illustrated in FIG. 3 optionally includes high-speed random access memory and optionally also includes non-volatile memory, such as one or more magnetic disk storage devices, flash memory devices, or other non-volatile solid-state memory devices. Access to memory 192 by other components of the regimen monitor device 250, such as CPU(s) 274 is, optionally, controlled by the memory controller 368.

In some embodiments, the memory 192 of the regimen monitor device 250 illustrated in FIG. 3 optionally includes a third data set 246 comprising a plurality of physiological measurements, and each such physiological measurement 247 includes a measurement value 248. In some embodiments, the physiological measurement 247 is body temperature of the subject. In some embodiments, the physiological measurement 247 is a measurement of activity of the subject. In some embodiments, these physiological measurements serve as an additional glycaemic risk measure. In some embodiments, the optional accelerometer 317, optional GPS 319, and/or magnetometer (not shown) of the regimen monitor device 250 or such components optionally within the one or more glucose monitors 102 and/or the one or more pens 104 is used to acquire such physiological measurements 247.

The peripherals interface 370 can be used to couple input and output peripherals of the device to CPU(s) 274 and memory 192. The one or more processors 274 run or execute various software programs and/or sets of instructions stored in memory 192, such as the insulin regimen monitoring module 204, to perform various functions for the regimen monitor device 250 and to process data.

In some embodiments, the peripherals interface 370, CPU(s) 274, and memory controller 368 are, optionally, implemented on a single chip. In some other embodiments, they are, optionally, implemented on separate chips.

RF (radio frequency) circuitry of network interface 284 receives and sends RF signals, also called electromagnetic signals. In some embodiments, the first data structure 210, the first data set 228, the plurality of glycaemic risk measurements 234, the optional second data set 238 and/or the optional third data set 246 is received using this RF circuitry from one or more devices such as a glucose sensor 102 associated with a subject, an insulin pen 104 associated with the subject and/or the data collection device 200. In some embodiments, the RF circuitry 108 converts electrical signals to/from electromagnetic signals and communicates with communications networks and other communications devices, glucose sensors 102, and insulin pens 104 and/or the data collection device 200 via the electromagnetic signals. The RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the regimen monitor device 250. The audio circuitry 372 receives audio data from peripherals interface 370, converts the audio data to electrical signals, and transmits the electrical signals to speaker 360. The speaker 360 converts the electrical signals to human-audible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 192 and/or the RF circuitry 284 by the peripherals interface 370.

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the regimen monitor device 250 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the regimen monitor device 250, opposite the display 282 on the front of the regimen monitor device 250, so that the input 280 is enabled for use as a viewfinder for still and/or video image acquisition. In some embodiments, another optical sensor 373 is located on the front of the regimen monitor device 250 so that the subject's image is obtained (e.g., to verify the health or condition of the subject, to determine the physical activity level of the subject, or to help diagnose a subject's condition remotely, to acquire visual physiological measurements 247 of the subject, etc.).

As illustrated in FIG. 3, a regimen monitor device 250 preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the regimen monitor device 250 is a smart phone. In other embodiments, the regimen monitor device 250 is not a smart phone but rather is a tablet computer, desktop computer, emergency vehicle computer, or other form or wired or wireless networked device. In some embodiments, the regimen monitor device 250 has any or all of the circuitry, hardware components, and software components found in the regimen monitor device 250 depicted in FIG. 2 or 3. In the interest of brevity and clarity, only a few of the possible components of the regimen monitor device 250 are shown in order to better emphasize the additional software modules that are installed on the regimen monitor device 250.

While the system 48 disclosed in FIG. 1 can work standalone, in some embodiments it can also be linked with electronic medical records to exchange information in any way.

Now that details of a system 48 for autonomously adjusting a long acting insulin medicament dosage in a prescribed insulin regimen for a subject have been disclosed, details regarding a flow chart of processes and features of the system, in accordance with an embodiment of the present disclosure, are disclosed with reference to FIGS. 4A through 4E. In some embodiments, such processes and features of the system are carried out by the insulin regimen monitoring module 204 illustrated in FIGS. 2 and 3.

Block 402.

With reference to block 402 of FIG. 4A, the goal of insulin therapy in subjects with either type 1 diabetes mellitus or type 2 diabetes mellitus is to match as closely as possible normal physiologic insulin secretion to control fasting and postprandial plasma glucose. As illustrated in FIG. 2, a monitoring device 250 comprises one or more processors 274 and a memory 192/290. The memory stores instructions that, when executed by the one or more processors, perform a method. In the method, a first data set 228 is obtained. The first data set 228 comprises glucose measurements 230 of the subject from one or more glucose sensors 102. FIG. 2 illustrates. Each such glucose measurement 230 is timestamped with a glucose measurement timestamp 232 to represent when the respective measurement was made.

In some embodiments, the glucose measurements 230 are autonomously measured. The FREESTYLE LIBRE CGM by ABBOTT ("LIBRE") is an example of a glucose sensor that may be used as a glucose sensor 102 in order to make autonomous glucose measurements of a subject. The LIBRE allows calibration-free glucose measurements with an on-skin coin-sized sensor, which can send up to eight hours of data to a reader device (e.g., the data collection device 200 and/or the regimen monitor device 250) via near field communications, when brought close together. The LIBRE can be worn for fourteen days in all daily life activities. Referring to block 404, in some embodiments, the glucose measurements are taken from the subject at an interval rate of 5 minutes or less, 3 minutes or less, or 1 minute or less. In some embodiments, the glucose measurements are taken from the subject at an interval rate of 5 minutes or less, 3 minutes or less, or 1 minute or less, over a time period of a day or more, two days or more, a week or more, or two weeks or more. In some embodiments, the glucose measurements are autonomously taken (e.g., without human effort, without human intervention, etc.). In some embodiments, the glucose measurements are manually taken (e.g., with manual human effort, with human intervention, etc.).

The regimen monitor device 250 accesses and/or stores a first data structure 210 that includes a prescribed insulin regimen 212 for the subject that is used to match as closely as possible normal physiologic insulin secretion to control fasting and postprandial plasma glucose. In the present disclosure, the prescribed insulin regimen 212 comprises a basal insulin medicament dosage regimen 214 that specifies the long acting insulin medicament dosage 216. The first data structure 210 further specifies an original target fasting blood glucose level 226 used as a basis to compute the long acting insulin medicament dosage.

In some embodiments, the long acting insulin medicament specified by the basal insulin medicament dosage regimen 214 consists of a single insulin medicament having a duration of action that is between 12 and 24 hours or a mixture of insulin medicaments that collectively have a duration of action that is between 12 and 24 hours. Examples of such long acting insulin medicaments include, but are not limited to Insulin Degludec (developed by NOVO NORDISK under the brand name Tresiba), NPH (Schmid, 2007, "New options in insulin therapy. J Pediatria (Rio J). 83(Suppl 5):S146-S155), Glargine (LANTUS, Mar. 2, 2007, insulin glargine [rDNA origin] injection, [prescribing information], Bridgewater, N.J.: Sanofi-Aventis), and Determir (Plank et al., 2005, "A double-blind, randomized, dose-response study investigating the pharmacodynamic and pharmacokinetic properties of the long-acting insulin analog detemir," Diabetes Care 28:1107-1112).

In some embodiments, the short acting insulin medicament specified by the bolus insulin medicament dosage regimen 220 comprises a single insulin medicament having a duration of action that is between three to eight hours or a mixture of insulin medicaments that collectively have a duration of action that is between three to eight hours. Examples of such short acting insulin medicaments include, but are not limited, to Lispro (HUMALOG, May 18, 2001, insulin lispro [rDNA origin] injection, [prescribing information], Indianapolis, Ind.: Eli Lilly and Company), Aspart (NOVOLOG, July 2011, insulin aspart [rDNA origin] injection, [prescribing information], Princeton, N.J., NOVO NORDISK Inc., July, 2011), Glulisine (Helms Kelley, 2009, "Insulin glulisine: an evaluation of its pharmacodynamic properties and clinical application," Ann Pharmacother 43:658-668), and Regular (Gerich, 2002, "Novel insulins: expanding options in diabetes management," Am J Med. 113:308-316).

Block 406.

Referring to block 406 of FIG. 4A, the method continues with the updating of a first glycaemic risk measure 236 of the subject. The first glycaemic risk measure is: (i) a total glucose level variability observed across the plurality of glucose measurements, (ii) a variability in a plurality of fasting glucose levels calculated from the plurality of glucose measurements, or (iii) a minimum glucose measurement observed in the plurality of glucose measurements, to name a few possible glycaemic risk measures. For instance, in some embodiments, the first glycaemic risk measure is a total glucose level variability observed across the plurality of glucose measurements. In some embodiments, the first glycaemic risk measure is a variability in a plurality of fasting glucose levels calculated from the plurality of glucose measurements. In some embodiments, the first glycaemic risk measure is a minimum glucose measurement observed in the plurality of glucose measurements.

In some embodiments, a larger set of glycaemic risk measures is considered. For instance, referring to block 408, in some embodiments the first data structure 210 further comprises an indication 218 as to when the subject is to inject the long acting insulin medicament dosage and the insulin regimen monitoring module 204 obtains a second data set 238 from one or more insulin pens 104 used by the subject to apply the prescribed insulin regimen. In such embodiments, it is possible to have a fuller set of glycaemic risk measures to draw upon for the fasting blood glucose target function. FIG. 2 illustrates. As illustrated in FIG. 2, the second data set 238 comprises insulin medicament records 240 over the time course. Each record 240 comprises: (i) an insulin medicament injection event 242 for an insulin medicament injection using an insulin pen 104 and (ii) a corresponding electronic timestamp 244 that is automatically generated by the respective pen upon occurrence of the event. Thus, in some such embodiments, the fasting blood glucose target function is based upon at least the first glycaemic risk measure and a second glycaemic risk measure, where the first glycaemic risk measure and the second glycaemic risk measure are each independently: (i) a total glucose level variability observed across the plurality of glucose measurements, (ii) a variability in a plurality of fasting glucose levels calculated from the plurality of glucose measurements, and (iii) a minimum glucose measurement observed in the plurality of glucose measurements, (iv) a rate of change in an insulin sensitivity factor calculated using the plurality of glucose measurements of the first data set 228 and the insulin medicament records 240 of the second data set 238, or (v) a basal adherence score over the time course that is computed by dividing (a) a number of insulin medicament injection events 242 that were taken by the subject when dictated by the basal insulin medicament dosage regimen 214 by (b) a total number of basal insulin medicament injection events dictated by the basal insulin medicament dosage regimen 214 in the time course.

In some such embodiments, the fasting blood glucose target function is based upon at least the first glycaemic risk measure, where the first glycaemic risk measure is: (i) a total glucose level variability observed across the plurality of glucose measurements, (ii) a variability in a plurality of fasting glucose levels calculated from the plurality of glucose measurements, (iii) a minimum glucose measurement observed in the plurality of glucose measurements, (iv) a rate of change in an insulin sensitivity factor calculated using the plurality of glucose measurements of the first data set 228 and the insulin medicament records 240 of the second data set 238, or (v) a basal adherence score over the time course that is computed by dividing (a) a number of insulin medicament injection events 242 that were taken by the subject when dictated by the basal insulin medicament dosage regimen 214 by (b) a total number of basal insulin medicament injection events dictated by the basal insulin medicament dosage regimen 214 in the time course.

Referring to block 410 of FIG. 4B, in some embodiments, the regimen monitor device 250 comprises a wireless receiver 284, and the first data set 228 is obtained wirelessly from a glucose sensor 102 affixed to the subject and/or the second data set 238 is obtained wirelessly from the one or more insulin pens 104.

As noted above, in some embodiments, one possible glycaemic risk measure 236 is the total glucose level variability observed across the plurality of glucose measurements. In more detail, referring to block 412 of FIG. 4B, in some embodiments a glycaemic risk measure (e.g., a first glycaemic risk measure or a second glycaemic risk measure, etc. used to compute the fasting blood glucose target function) is the total glucose level variability observed across the plurality of glucose measurements computed as one of (i), (ii), (iii), or (iv): (i) a range of total glucose levels in the plurality of glucose levels in the first data set 228, (ii) an interquartile range of glucose levels in the plurality of glucose levels in the first data set 228, (iii) an average squared difference of the glucose levels in the plurality of glucose levels from the mean (µ) of the plurality of glucose levels ($\sigma^2$) in the first data set 228 computed as:

$$\sigma^2 = \frac{\sum_{i}^{P}(m_i - \mu)^2}{P}$$

where, $m_i$ is the $i^{th}$ glucose levels in the plurality of glucose levels in the first data set 228, and P is the number of glucose levels in the plurality of glucose levels in the first data set 228, and (iv) the standard deviation of the glucose levels in the plurality of glucose levels in the first data set 228 computed as $\sqrt{\sigma^2}$.

In some embodiments, the plurality of glucose levels in the first data set 228 (e.g., the value P) is limited to glucose levels measured from the subject in the past four hours, the past twelve hours, the past 24 hours, the past two days, the past week, or the past two weeks. In other words, in some embodiments, the first data set 228 only has glucose measurements for the subject from the past four hours, the past twelve hours, the past 24 hours, the past two days, the past week, or the past two weeks. In other embodiments, the first data set 228 has glucose measurements for the subject for more than the past four hours, the past twelve hours, the past 24 hours, the past two days, the past week, or the past two weeks, but measurements that are older than the past four hours, the past twelve hours, the past 24 hours, the past two days, the past week, or the past two weeks are not used to calculate total glucose level variability observed across the plurality of glucose measurements of the subject.

As noted above, in some embodiments, a glycaemic risk measure 236 (e.g., the first glycaemic risk measure, the second glycaemic risk measure, etc.) used in the computation of the fasting blood glucose target function is the variability in a plurality of fasting glucose levels calculated from the plurality of glucose measurements. In more detail, referring to block 414 of FIG. 4B, in some embodiments the glycaemic risk measure is the variability in a plurality of fasting glucose levels calculated from the plurality of glucose measurements computed as one of (i), (ii), (iii), or (iv): (i) a range of fasting glucose levels in the plurality of fasting glucose levels, (ii) an interquartile range of fasting glucose levels in the plurality of fasting glucose levels, (iii) an average squared difference of the fasting glucose levels in the plurality of fasting glucose levels from the mean (µ) of the plurality of fasting glucose levels ($\sigma^2$) computed as:

$$\sigma^2 = \frac{\sum_{i}^{P}(m_i - \mu)^2}{P}$$

where, $m_i$ is the $i^{th}$ fasting glucose levels in the plurality of fasting glucose levels, and P is the number of fasting glucose levels in the plurality of fasting glucose levels, and (iv) the standard deviation of the fasting glucose levels in the plurality of fasting glucose levels computed as $\sqrt{\sigma^2}$.

In some embodiments, the number of fasting glucose levels in the plurality of fasting glucose levels from the first data set 228 (e.g., the value P) is limited to fasting glucose levels measured from the subject in the past four hours, the past twelve hours, the past 24 hours, the past two days, the past week, or the past two weeks. In other words, in some embodiments, the first data set 228 only has glucose measurements for the subject from the past four hours, the past twelve hours, the past 24 hours, the past two days, the past week, or the past two weeks that are used to determine the occurrence of the fasting glucose levels in the plurality of fasting glucose levels. In other embodiments, the first data set 228 has glucose measurements for the subject for more than the past four hours, the past twelve hours, the past 24 hours, the past two days, the past week, or the past two weeks, but measurements that are older than the past four hours, the past twelve hours, the past 24 hours, the past two days, the past week, or the past two weeks are not used to determine the fasting glucose levels in the plurality of fasting glucose levels that, in turn, are used to calculate the variability in the plurality of fasting glucose levels.

In some embodiments, the plurality of fasting glucose levels are determined by first autonomously detecting fasting events using a fasting detection algorithm and the glucose measurements 230 in the first data set 228. There are a number of methods for detecting a fasting event using glucose measurements 230 from a glucose monitor 102. For instance, in some embodiments a first fasting event is identified in a first time period (e.g., a period of 24 hours) encompassed by the plurality of glucose measurements in the first data set 228 by first computing a moving period of variance $\sigma_k^2$ across the glucose measurements, where:

$$\sigma_k^2 = \left(\frac{1}{M}\sum_{i=k-M}^{k}(G_i - \overline{G})\right)^2$$

and where, $G_i$ is the $i^{th}$ glucose measurement in the portion k of the plurality of glucose measurements considered, M is a number of glucose measurements in the plurality of glucose measurements and represents a contiguous predetermined time span, $\overline{G}$ is the mean of the M glucose measurements selected from the plurality of glucose measurements of the first data set 228, and k is within the first time period. As an example, the glucose measurements may span several days or weeks, with glucose measurements taken every five minutes. A first time period k (e.g., one day) within this overall time span is selected and thus the portion k of the plurality of measurements is examined for a period of minimum variance. The first fasting period is deemed to be the period of minimum variance $$\min_{k} \sigma_k^2$$

within the first time period. Next, the process is repeated with portion k of the plurality of glucose measurements by examining the next portion k of the plurality of glucose measurements for another period of minimum variance thereby assigning another fasting period.

Moreover, in some embodiments, only those fasting events that are deemed basal insulin medicament dosage regimen 206 adherent are used to calculate fasting glucose levels. Example 3, below, illustrates a way in which a determination is made as to whether a fasting event is basal insulin medicament dosage regimen 206 adherent. Moreover, European Patent Application Number EP16177080.5, entitled "Regimen Adherence Measure for Insulin Treatment Base on Glucose Measurement and Insulin Pen Data," filed Jun. 30, 2016, which is hereby incorporated by reference, discloses techniques for identifying and classifying fasting events as adherent or nonadherent. In some embodiments, only those fasting events that are classified as "basal regimen adherent" in accordance with European Patent Application Number EP16177080.5 are used to calculate fasting glucose levels in the present disclosure. In some embodiments, there is more than one glucose measurement 230 for a given fasting event encompassed by the first data set 230. When this is the case, the fasting blood glucose value for this fasting event is taken as an average value, or some other measure of central tendency, of the glucose measurements 230 within the time period.

Block 416.

Figure 8:
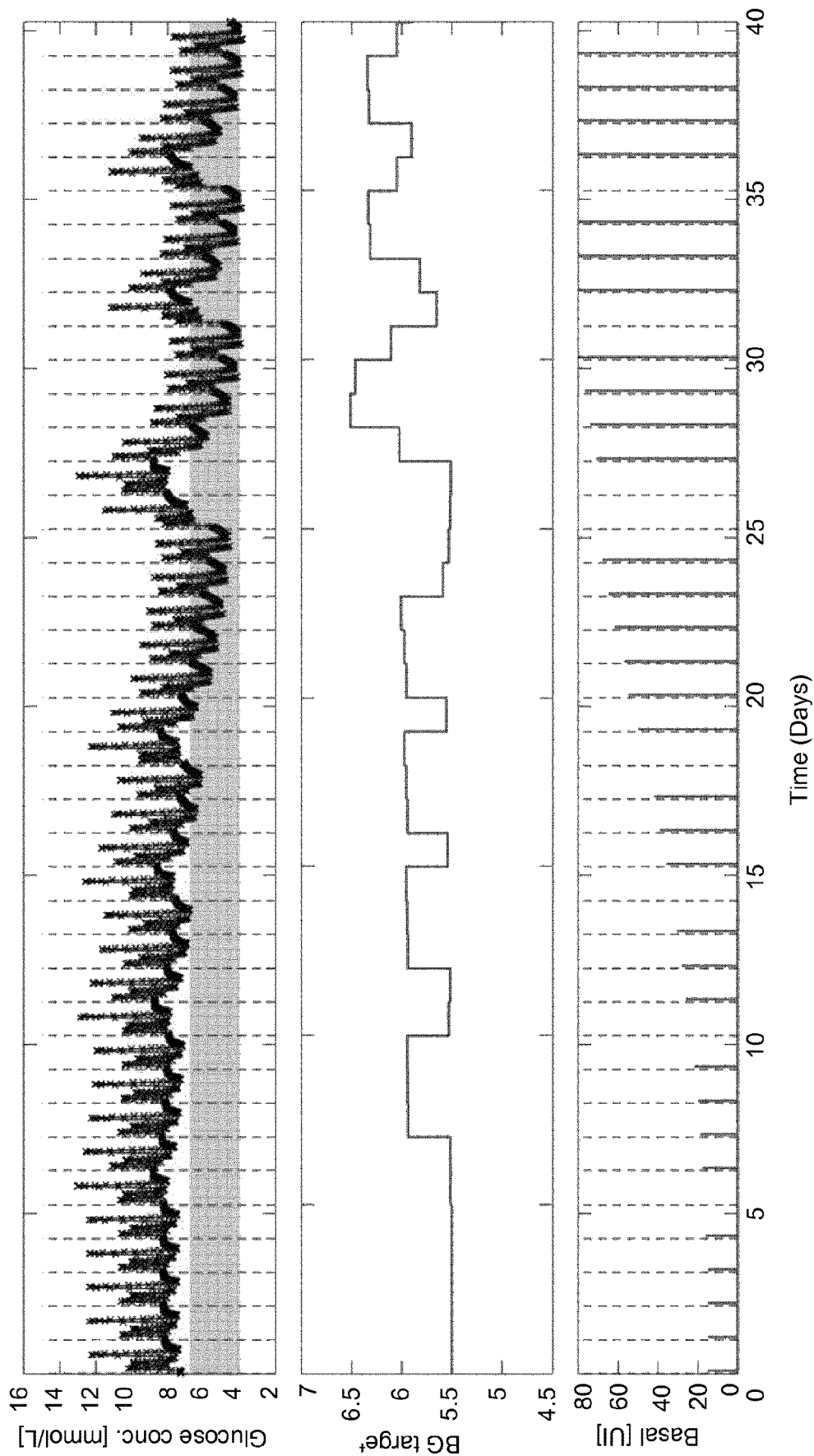
FIG. 8 illustrates an example simulation of a titrator, with a variable glucose target, for titrating a type 2 diabetic patient over 40 days, in accordance with the present disclosure. The top panel shows blood glucose concentration during basal titration over the 40 days. Every few days the patient forgets to take his basal. The basal titration with a variable glucose target avoids hypoglycaemic events in the simulation.
Figure 9:
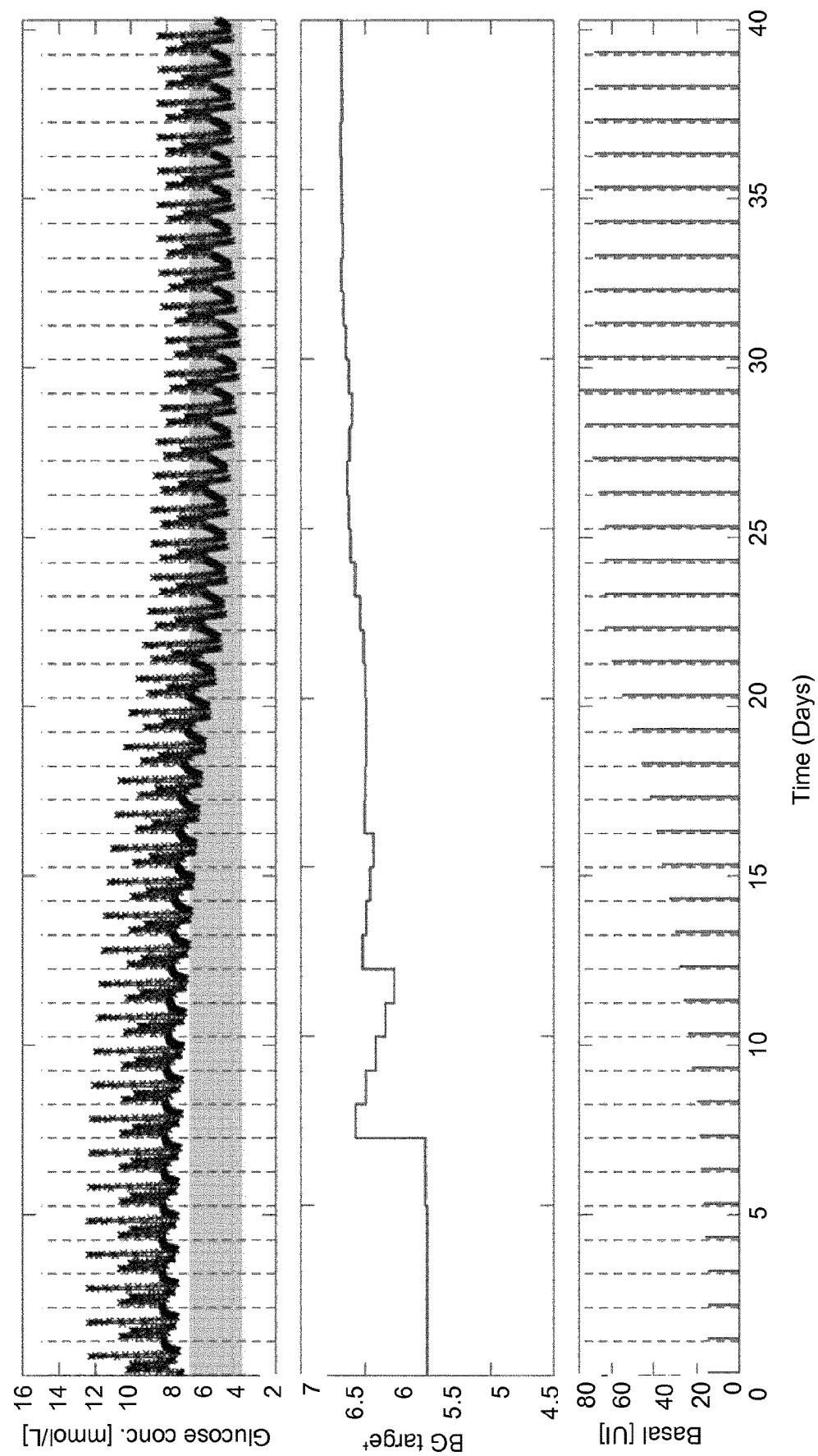
FIG. 9 illustrates an example simulation of a titrator, with a variable glucose target, for titrating a type 2 diabetic patient over 40 days, in accordance with the present disclosure. The top panel shows blood glucose concentration during basal titration over the 40 days. Every few days the fasting glucose measurement is too high due to some unknown reason. The basal titration with a variable glucose target avoids hypoglycaemic events in the simulation.

Referring to block 416 of FIG. 4C, the method continues with the computation of a fasting blood glucose target function that is based upon at least the first glycaemic risk measure thereby obtaining an updated target fasting blood glucose level that is between the minimum target fasting blood glucose level (226) and the maximum target fasting blood glucose level (227). FIGS. 8 and 9 illustrate.

FIG. 8 illustrates an example simulation of a titrator, with a variable glucose target, for titrating a type 2 diabetic patient over 40 days, in accordance with the present disclosure. The fasting blood glucose target function calculates the updated (variable) target fasting blood glucose level as a function of the combination comprising: (i) the first glycaemic risk measure and (ii) the second glycaemic risk measure. For FIG. 8, the fasting blood glucose target function comprising (i) the first glycaemic risk measure and (ii) the second glycaemic risk measure is a linear function of minimum blood glucose over the past three days (the first glycaemic risk measure) and variations in blood glucose over the past three days (the second glycaemic risk measure) and basal adherence over the past three days (a third glycaemic risk measure). Thus, FIG. 8 illustrates that computing a fasting blood glucose target function that is based upon at least the first glycaemic risk measure may, in fact, be based upon a combination of more than just one glycaemic risk measure. In some embodiments, the fasting blood glucose target function uses a combination of three or more glycaemic risk measures, four or more glycaemic risk measures or five or more glycaemic risk measures 236. In some embodiments, the fasting blood glucose target function makes use of a plurality of glycaemic risk measures expressed as a linear combination. In some embodiments, the fasting blood glucose target function makes use of a plurality of glycaemic risk measures expressed as a nonlinear combination. In FIG. 8, the top panel shows blood glucose concentration during basal titration over the 40 days. Every few days the patient forgets to take his basal. The basal titration with a variable target fasting blood glucose level computed using the fasting blood glucose target function avoids hypoglycaemic events in the simulation.

FIG. 9 illustrates another example simulation of a titrator, with a variable target fasting blood glucose level 225 computed using a fasting blood glucose target function, for titrating a type 2 diabetic patient over 40 days, in accordance with the present disclosure. In this example, the fasting blood glucose target function is based upon (i) a first glycaemic risk measure and (ii) a second glycaemic risk measure and the fasting blood glucose target function provides an updated target fasting blood glucose level that is between the minimum target fasting blood glucose level (226) and the maximum target fasting blood glucose level (227). For FIG. 9, the fasting blood glucose target function is based upon (i) the first glycaemic risk measure and (ii) the second glycaemic risk measure is a linear function of (a) minimum blood glucose over the past three days, (b) variations in fasting blood glucose over the past three days, (c) changes in insulin sensitivity factor estimation and (d) basal adherence past three days. Thus, FIG. 9 illustrates an example where the fasting blood glucose target function is based upon a combination of four glycaemic risk measures. In FIG. 9, the top panel shows blood glucose concentration during basal titration over the 40 days. Every few days the fasting glucose measurement is fifty percent too high due to some unknown reason. The basal titration with a variable glucose target avoids hypoglycaemic events in the simulation.

Block 418 of FIG. 4C illustrates an embodiment of computing a fasting blood glucose target function that is based upon at least the first glycaemic risk measure thereby obtaining an updated target fasting blood glucose level that is between the minimum target fasting blood glucose level (226) and the maximum target fasting blood glucose level (227).

A range of possible values for the first glycaemic risk measure and a range of possible values for the second glycaemic risk measure are each dimensions of an N-dimensional space ($\mathbb{R}^N$) (e.g., $\mathbb{R}^3$ if the fasting blood glucose target function is limited to the first and second glycaemic risk measures, where the third dimension is the calculated target fasting blood glucose level, but some higher dimension if the fasting blood glucose target function includes more than the first and second glycaemic risk measures). In this example, the fasting blood glucose target function has the form $\Sigma_i^{N-1} c_i x_i = c_R$. Here, $c_i$ is an $i^{th}$ constant applied to an $x_i^{th}$ glycaemic risk measure, and the $x_i^{th}$ glycaemic risk measure is in a plurality of glycaemic risk measures that includes the first glycaemic risk measure and the second glycaemic risk measure. Further, i is an integer between one and N−1, and FGL is the target fasting blood glucose level 225. Example 1 below provides an example of such a fasting blood glucose target function where N is two, and thus the fasting blood glucose target function relies upon a single glycaemic risk measure.

Block 420 of FIG. 4C illustrates an embodiment in which the fasting blood glucose target function is based upon a first glycaemic risk measure and a second glycaemic risk measure where the first glycaemic risk measure is the variability in the plurality of fasting glucose levels and the second glycaemic risk measure is the basal adherence score over the time course. A range of possible values for the first glycaemic risk measure and a range of possible values for the second glycaemic risk measure are each dimensions of an N dimensional space ($\mathbb{R}^3$), where the target fasting blood glucose level forms the third dimension. The fasting blood glucose target function has the form $c_1 x_1 + c_2 x_2 = FGL$ where $c_1$ is a constant applied to the first glycaemic risk measure, $c_2$ is a constant applied to the second glycaemic risk measure, and FGL is the target fasting blood glucose level that is determined.

In some embodiments, the fasting blood glucose target function is a nonlinear combination of glycaemic risk measures. Example 2 below illustrates.

Referring to block 422 of FIG. 4D, in some embodiments the first glycaemic risk measure is the variability in the plurality of fasting glucose levels, the second glycaemic risk measure is a function of the basal adherence score over the time course, and a third glycaemic risk measure is a function of the minimum glucose measurement in the plurality of glucose measurements of the subject. In such embodiments, the fasting blood glucose target function is a function of: (i) the variability in the plurality of fasting glucose levels as a first dimension of the 4-dimensional space, (ii) a function of the basal adherence score over the time course as a second dimension of the 4-dimensional space, and (iii) and a function of the minimum glucose measurement in the plurality of glucose measurements of the subject as a third dimension of the 4-dimensional space.

Block 424 is an example of an implementation of block 422 in accordance with one embodiment of the present disclosure. A range of possible values for the variability in the plurality of fasting glucose levels, a range of possible values for the basal adherence score, and a range of possible values for the minimum glucose measurement define a three dimensional space and the fasting blood glucose target function has the form form $c_1x+c_2y+c_3z=FGL$, where $c_1$, $c_2$ and $c_3$ are constants respectively applied to the variability in the plurality of fasting glucose levels, the basal adherence score over the time course, and the minimum glucose measurement, and FGL is the target fasting blood glucose level 225.

Referring to Block 426 of FIG. 4D, in some embodiments the method further comprises storing the new target fasting blood glucose level 225 in the first data structure 210 and the method of FIG. 4 is repeated on a recurring basis. In this way, the target glucose value is updated over time as illustrated in FIGS. 8 and 9.

Referring to block 428 of FIG. 4D, in some embodiments, the method further comprises autonomously obtaining one or more physiological measurements of the subject. In such embodiments, the fasting blood glucose target function is based upon at least the first glycaemic risk measure and a second glycaemic risk measure, where the first glycaemic risk measure and the second glycaemic risk measure are each independently: (i) a total glucose level variability observed across the plurality of glucose measurements, (ii) a variability in the plurality of fasting glucose levels calculated from the plurality of glucose measurements, (iii) the minimum glucose measurement observed in the plurality of glucose measurements, or (iv) the one or more physiological measurements of the subject. In some such embodiments each physiological measurement 247 in the one or more physiological measurements is a body temperature of the subject or a measurement of cardiovascular activity of the subject.

Referring to block 430 of FIG. 4E, in some embodiments, the method further comprises autonomously obtaining a third data set 246, the third data set comprising one or more physiological measurements of the subject. In such embodiments, the fasting blood glucose target function is based upon at least the first glycaemic risk measure, the second glycaemic risk measure and a third glycaemic risk measure, where the first glycaemic risk measure, the second glycaemic risk measure, and the third glycaemic risk measure are each independently: (i) a total glucose level variability observed across the plurality of glucose measurements, (ii) a variability in the plurality of fasting glucose levels calculated from the plurality of glucose measurements, (iii) a minimum glucose measurement observed in the plurality of glucose measurements, (iv) a rate of change in an insulin sensitivity factor calculated using the plurality of glucose measurements and the second data set, (v) a basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course, or (vi) the one or more physiological measurements of the subject. In some such embodiments each physiological measurement in the one or more physiological measurements is a body temperature of the subject or a measurement of cardiovascular activity of the subject.

Referring to block 432 of FIG. 4E, with the target fasting blood glucose level for the prescribed insulin regimen now updated, it is now possible to adjust the long acting insulin medicament dosage 216. In some embodiments the long acting insulin medicament dosage is computed using the target fasting blood glucose level by an equation of the form:

$$ND = \frac{BG_{meas} - FGL}{ISF}$$

where ND is the next basal dose 216, $BG_{meas}$ is a calculate fasting blood glucose level from the glucose measurements 230, FGL is the calculated fasting glucose target, as described in the present disclosure, and ISF is an estimated basal insulin sensitivity factor of the subject.

Example 1

Figure 10:
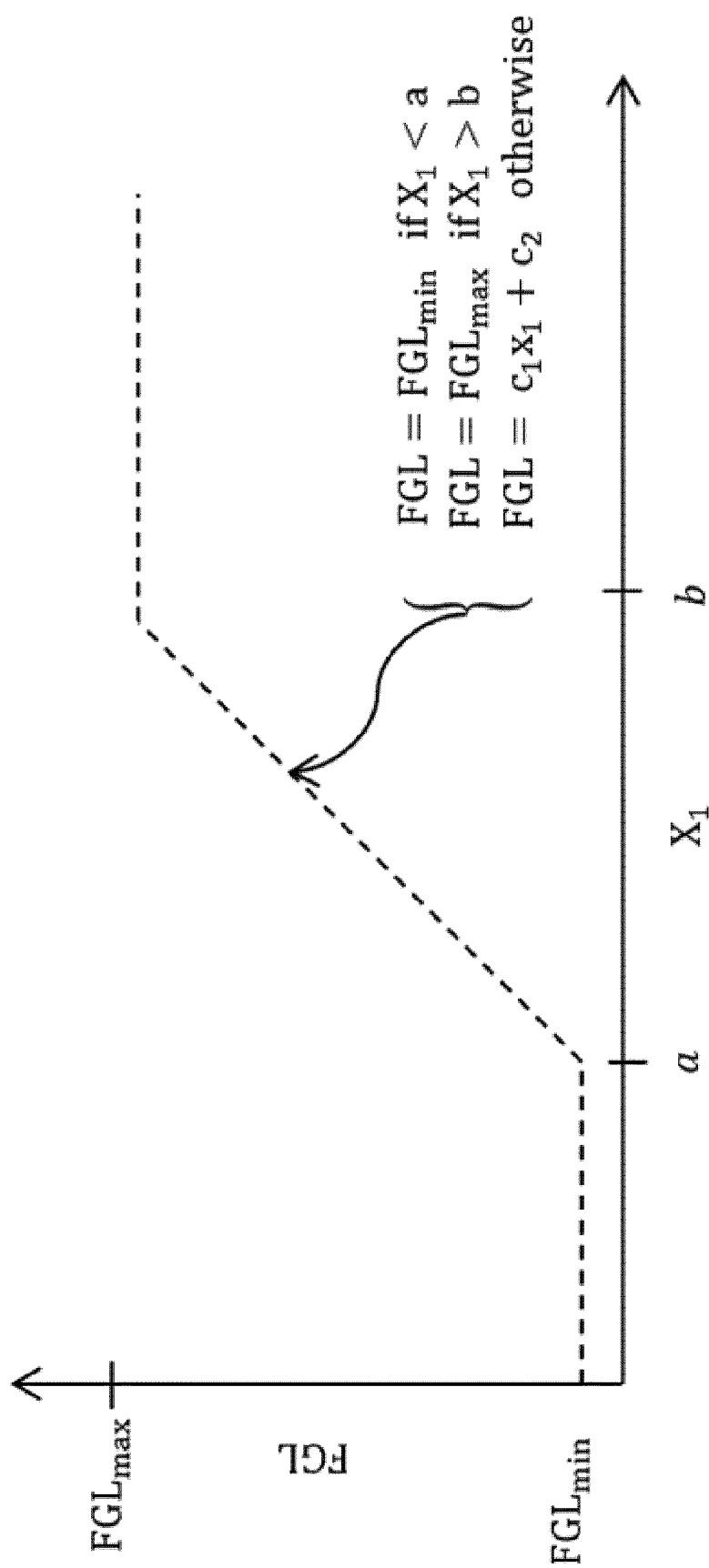
FIG. 10 illustrates a fasting blood glucose target function of the form $c_1 x_1 + c_2 = FGL$, where the first glycaemic risk measure of the subject is updated to obtain a value $x_1$ which, in turn, is used to compute the fasting blood glucose target function $c_1 x_1 + c_2 = FGL$ and therefore obtain an updated target fasting blood glucose level that is between a minimum target fasting blood glucose level and a maximum target fasting blood glucose level ($FGL_{min}$ and $FGL_{max}$, respectively), in accordance with an embodiment of the present disclosure.

This example provides a fasting blood glucose target function where a single glycaemic risk measure is used and the fasting blood glucose target function has the form:

$c_1x_1+c_2=FGL$ where, for example, $x_1$ is the first glycaemic risk measure. FIG. 10 illustrates the $c_1x_1+c_2=FGL$ the fasting blood glucose target function. The first glycaemic risk measure 236 of the subject is updated (e.g., as set forth in block 406) to obtain a value $x_1$. This value $x_1$ is then used to compute the fasting blood glucose target function $c_1x_1+c_2=FGL$ and therefore obtain the updated target fasting blood glucose level 225 that is between the minimum target fasting blood glucose level 226 and the maximum target fasting blood glucose level 227 ($FGL_{min}$ 226 and $FGL_{max}$ 227, respectively).

Example 2

Figure 11:
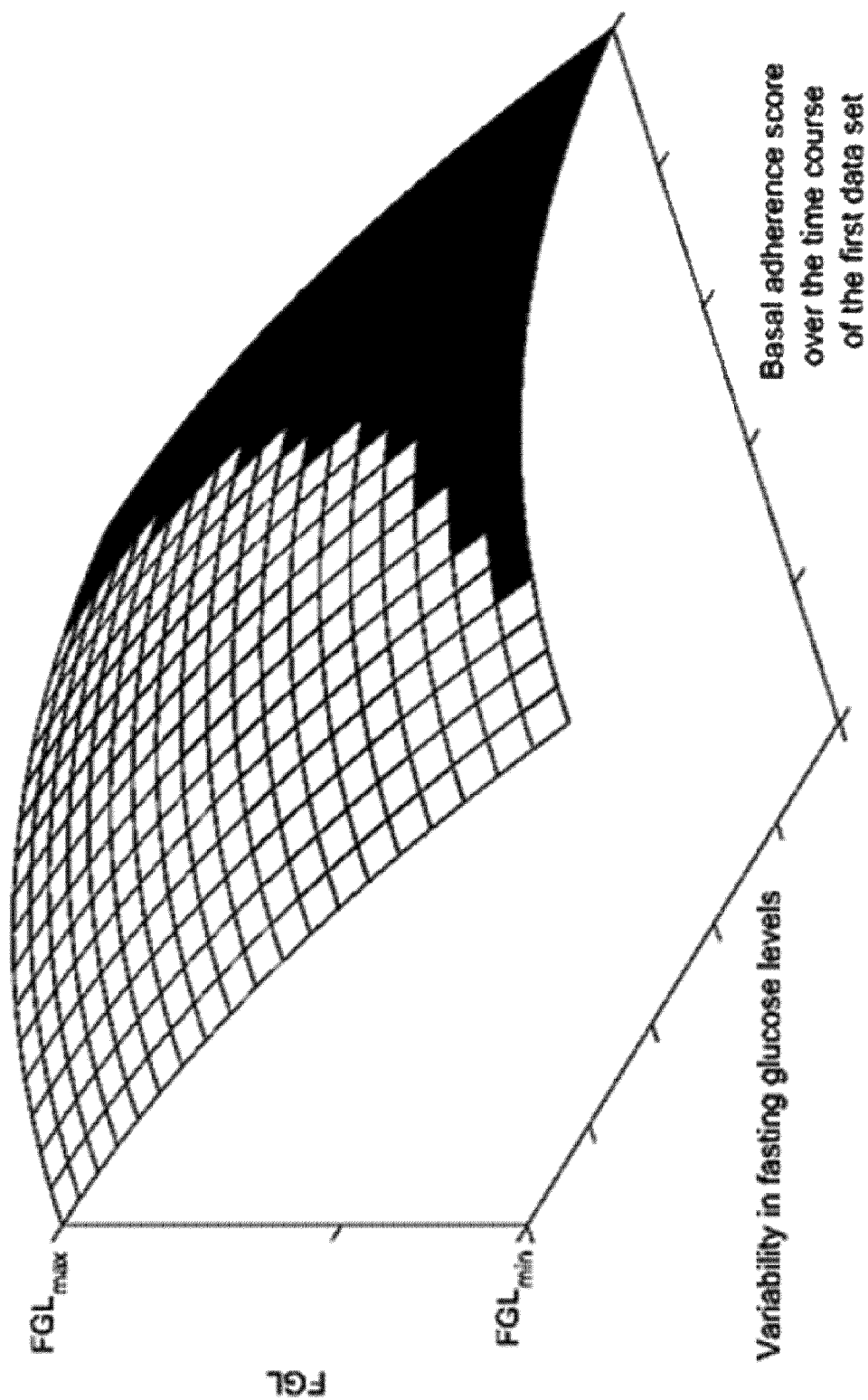
FIG. 11 illustrates an embodiment in which a nonlinear fasting blood glucose target function is based upon a first glycaemic risk measure and a second glycaemic risk measure. Here, the first glycaemic risk measure is variability in fasting glucose levels and the second glycaemic risk measure is basal adherence score over the time course of the first data set. The nonlinear fasting blood glucose target function is adapted to express an increasing FGL with an increasing glycaemic risk measure, in accordance with an embodiment of the present disclosure.

In some embodiments, the fasting blood glucose target function is a linear or nonlinear combination of glycaemic risk measures. FIG. 11 illustrates an embodiment in which the nonlinear fasting blood glucose target function is based upon variability in fasting glucose levels and basal insulin regimen adherence score over the time course of the first data set. Alternatively, the variability in fasting glucose level is expressed as a function of a first glycaemic risk measure, and the basal adherence score over the time course of the first data set is expressed as a function of the second glycaemic risk measure, where the functions are adapted to express an increasing FGL with an increasing glycaemic risk measure, e.g., FGL is an increasing function of a glycaemic risk measure.

In FIG. 11, the less variability observed in the fasting glucose levels, the lower FGL can be set. In other words, reduced variability in fasting glucose levels connotes confidence in the patient's treatment status and thus allows for more aggressive insulin medicament treatment. Conversely, in FIG. 11, the lower the basal insulin regimen adherence score is over the time course of the first data set, the higher the FGL must be set. In other words, lower basal insulin regimen adherence scores connote a lack of confidence in the patient's adherence to their insulin regimen and thus warrants for less aggressive (more conservative) insulin medicament treatment. Advantageously, the fasting blood glucose target function allows for the concurrent use of these two glycaemic risk measures even though they provide opposing influences on the calculated value of FGL. For instance, in some embodiments, a fasting blood glucose target function for FIG. 11 has the form $\Sigma_i^2 f_i(x_i)$=FGL where, $f_1$ is a function of the variability in fasting glucose levels ($x_1$) and $f_2$ is a function of the basal insulin regimen adherence score over the time course of the first data set ($x_2$) and where $f_1$ and $f_2$ are different functions. As such, a range of possible values for the first glycaemic risk measure and a range of possible values for the second glycaemic risk measure are each dimensions of an N dimensional space ($\mathbb{R}^3$), where the target fasting blood glucose level forms the third dimension. The first glycaemic risk measure and the second glycaemic risk measure are updated in accordance with block 406 and these updated values are used to compute the fasting blood glucose target function and thereby obtain a value for the target fasting blood glucose level 225.

Example 3: Use of Glucose Measurements to Determine Whether a Fasting Event is Insulin Regimen Adherent In some embodiments, the first data set 228 comprising a plurality of glucose measurements is obtained. In some embodiments the glucose measurements are obtain autonomously, for instance by a continuous glucose monitor 102. In this example, in addition to the autonomous glucose measurements, insulin administration events are obtained in the form of insulin medicament records 240 from one or more insulin pens 104 used by the subject to apply the prescribed insulin regimen 212. These insulin medicament records 240 may be in any format, and in fact may be spread across multiple files or data structures. As such, in some embodiments, the instant disclosure leverages the recent advances of insulin administration pens, which have become "smart" in the sense that they can remember the timing and the amount of insulin medicament administered in the past. One example of such an insulin pen 104 is the NovoPen 5. Such pens assists patients in logging doses and prevent double dosing. It is contemplated that insulin pens will be able to send and receive insulin medicament dose volume and timing, thus allowing the integration of continuous glucose monitors 102, insulin pens 104 and the algorithms of the present disclosure. As such, insulin medicament records 240 from one or more insulin pens 104 is contemplated, including the wireless acquisition of such data from the one or more insulin pens 104.

In some embodiments, each insulin medicament record 240 comprises: (i) a respective insulin medicament injection event 242 including an amount of insulin medicament injected into the subject using a respective insulin pen in the one or more insulin pens and (ii) a corresponding electronic timestamp 244 that is automatically generated by the respective insulin pen 104 upon occurrence of the respective insulin medicament injection event.

In some embodiments, a fasting event is identified using the glucose measurements 230 of the subject and their associated glucose measurement timestamps 232 in the first data set 228. Once a fasting event is identified, by the method described for block 414 above, or any other method, a classification is applied to the fasting event. The classification is one of "insulin regimen adherent" and "insulin regimen nonadherent."

A fasting event is deemed insulin regimen adherent when the acquired one or more medicament records establish, on a temporal and quantitative basis, adherence with the basil insulin medicament regimen 214 during the fasting event. A fasting event is deemed insulin regimen nonadherent when the acquired one or more medicament records 240 do not include one or more medicament records that establish, on a temporal and quantitative basis, adherence with the basal insulin medicament dosage regimen 214 during the fasting event. In some embodiments the basal insulin medicament dosage regimen 214 specifies that a dose of long acting insulin medicament 216 is to be taken during each respective epoch 218 in a plurality of epochs and that a fasting event is deemed insulin regimen nonadherent when there are no medicament records for the epoch 218 associated with the fasting event. In various embodiments, each epoch in the plurality of epochs is two days or less, one day or less, or 12 hours or less. Thus, consider the case where the first data set 228 is used to identify a fasting period and the basal insulin medicament regimen 214 specifies to take dosage A of a long acting insulin medicament 216 every 24 hours. In this example, therefore, the epoch is one day (24 hours). The fasting event is inherently timestamped because it is derived from a period of minimum variance in timestamped glucose measurements, or by other forms of analysis of the timestamped glucose measurements 230. Thus the timestamp, or period of fasting, represented by a respective fasting event is used as a starting point for examining whether the fasting event is insulin regimen adherent. For instance, if the period of fasting associated with the respective timestamp is 6:00 AM on Tuesday, May 17, what is sought in the insulin medicament injection records 240 is evidence that the subject took dosage A of the long acting insulin medicament in the 24 hour period (the epoch) leading up to 6:00 AM on Tuesday, May 17 (and not more or less of the prescribed dosage). If the subject took the prescribed dosage of the long acting insulin medicament during this epoch, the fasting event (and/or the basal injection event and/or the glucose measurements during this time) is deemed insulin regimen adherent. If the subject did not take the dose of the long acting insulin medicament 216 during this epoch 218 (or took more than the dose of the long acting insulin medicament during this period specified by the long acting insulin regimen 216), the fasting event (and/or the basal injection event and/or the glucose measurements during this time) is deemed to be insulin regimen nonadherent.

In some embodiments, the epoch is defined by the basal insulin medicament dosage regimen 214 and, so long as the subject took the amount of long acting insulin required by the basal insulin medicament dosage regimen 214 during the epoch (and not more), even if after the fasting event, the fasting event will be deemed insulin regimen adherent. For instance, if the epoch is one day beginning each day at just after midnight (in other words the basal insulin medicament dosage regimen 214 specifies one or more long acting insulin medicament dosages to be taken each day, and further defines a day as beginning and ending at midnight), and the fasting event occurs at noon, the fasting event will be deemed insulin regimen adherent provided that the subject takes the long acting insulin medicament injections prescribed for the day at some point during the day.

LIST OF EMBODIMENTS

1. A device (250) for autonomously adjusting a long acting insulin medicament dosage (216) in a prescribed insulin regimen for a subject, wherein the device comprises one or more processors (274) and a memory (192/290), the memory comprising:
  a first data structure (210) that includes the prescribed insulin regimen (212) including a basal insulin medicament dosage regimen (214), wherein the basal insulin medicament dosage regimen specifies the long acting insulin medicament dosage and wherein the first data structure further comprises (i) a target fasting blood glucose level (225), (ii) a minimum target fasting blood glucose level (226) and (iii) a maximum target fasting blood glucose level (227), and
  instructions that, when executed by the one or more processors, perform a method of:
  obtaining a first data set (228), the first data set comprising a plurality of glucose measurements of the subject taken over a time course and, for each respective glucose measurement (230) in the plurality of glucose measurements, a corresponding timestamp (232) representing when in the time course the respective glucose measurement was made;
  updating a first glycaemic risk measure (236), wherein the first glycaemic risk measure is:
    (i) a total glucose level variability observed across the plurality of glucose measurements,
    (ii) a variability in a plurality of fasting glucose levels calculated from the plurality of glucose measurements, or
    (iii) a minimum glucose measurement observed in the plurality of glucose measurements; and
  computing a fasting blood glucose target function that is based upon at least the first glycaemic risk measure thereby obtaining an updated target fasting blood glucose level that is between the minimum target fasting blood glucose level (226) and the maximum target fasting blood glucose level (227); and
  adjusting the long acting insulin medicament dosage based upon the updated target fasting blood glucose level.

2. The device of embodiment 1, wherein
  the first data structure further comprises an indication (218) as to when the subject is to inject the long acting insulin medicament dosage, and
  the method further comprises:
  obtaining a second data set (238) from one or more insulin pens used by the subject to apply the prescribed insulin regimen, the second data set comprising a plurality of insulin medicament records over the time course, each insulin medicament record (240) in the plurality of medicament records comprising: (i) a respective insulin medicament injection event (242) representing an insulin medicament injection into the subject using a respective insulin pen in the one or more insulin pens (104) and (ii) a corresponding electronic timestamp (244) that is automatically generated by the respective insulin pen upon occurrence of the respective insulin medicament injection event; and
  the fasting blood glucose target function is based upon at least the first glycaemic risk measure and a second glycaemic risk measure, wherein the first glycaemic risk measure and the second glycaemic risk measure are each independently:
    (i) the total glucose level variability observed across the plurality of glucose measurements,
    (ii) the variability in the plurality of fasting glucose levels calculated from the plurality of glucose measurements,
    (iii) the minimum glucose measurement observed in the plurality of glucose measurements,
    (iv) a rate of change in an insulin sensitivity factor calculated using the plurality of glucose measurements and the second data set, or
    (v) a basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course.

3. The device of embodiment 2, wherein a range of possible values for the first glycaemic risk measure and a range of possible values for the second glycaemic risk measure are each dimensions of an N-dimensional space ($\mathbb{R}^N$) and the fasting blood glucose target function has the form:

$$\Sigma_i^{N-1} c_i x_i = FGL$$

wherein,
  $c_i$ is an $i^{th}$ constant applied to an $x_i^{th}$ glycaemic risk measure, wherein the $x_i^{th}$ glycaemic risk measure is in a plurality of glycaemic risk measures that includes the first glycaemic risk measure and the second glycaemic risk measure, and wherein i is an integer between one and N−1; and
  FGL is the target fasting blood glucose level.

4. The device of embodiment 2,
  the first glycaemic risk measure is the variability in the plurality of fasting glucose levels,
  the second glycaemic risk measure is the basal adherence score over the time course, and,
  a range of possible values for the first glycaemic risk measure and a range of possible values for the second glycaemic risk measure are each dimensions of an N-dimensional space ($\mathbb{R}^N$) and the fasting blood glucose target function has the form:

$$c_1 x_1 + c_2 x_2 = FGL$$

wherein,
  $c_1$ is a constant applied to the first glycaemic risk measure,
  $c_2$ is a constant applied to the second glycaemic risk measure, and
  FGL is the target fasting blood glucose level.

5. The device of embodiment 2, wherein
  the first glycaemic risk measure is the variability in the plurality of fasting glucose levels,
  the second glycaemic risk measure is the basal adherence score over the time course, and,
  a third glycaemic risk measure is the minimum glucose measurement in the plurality of glucose measurements of the subject, and
  the fasting blood glucose target function is a function of:
    (i) the variability in the plurality of fasting glucose levels as a first dimension of the N-dimensional space,
    (ii) the basal adherence score over the time course as a second dimension of the N-dimensional space, and (iii)

and the minimum glucose measurement in the plurality of glucose measurements of the subject as a third dimension of the N-dimensional space.

6. The device of embodiment 5 wherein a range of possible values for the variability in the plurality of fasting glucose levels define a first dimension a three-dimensional space ($\mathbb{R}^3$), a range of possible values for the basal adherence score over the time course define a second dimension in the three-dimensional space, and a range of possible values for the minimum glucose measurement define a third-dimension in the three dimensional space, and the fasting blood glucose target function has the form:

$$c_1 x + c_2 y + c_3 z = FGL$$

wherein,
$c_1$ is a first constant applied to the variability in the plurality of fasting glucose levels,
$c_2$ is a second constant applied to the basal adherence score over the time course,
$c_3$ is a third constant applied to the minimum glucose measurement, and
FGL is the target fasting blood glucose level.

7. The device of any one of embodiments 1-6, wherein the method further comprises:
storing the updated target fasting blood glucose level in the first data structure and wherein
the method is repeated on a recurring basis.

8. The device of any one of embodiments 1-7, wherein successive measurements in the plurality of glucose measurements are autonomously taken from the subject at an interval rate of 5 minutes or less, 3 minutes or less, or 1 minute or less.

9. The device of embodiment 2, wherein the device further comprises a wireless receiver (284), and wherein the first data set is obtained wirelessly from a glucose sensor (102) affixed to the subject and/or the second data set is obtained wirelessly from the one or more insulin pens (104).

10. The device of any one of embodiments 2-3, wherein the first glycaemic risk measure or the second glycaemic risk measure is the total glucose level variability observed across the plurality of glucose measurements computed as one of (i), (ii), (iii), or (iv):
(i) a range of total glucose levels in the plurality of glucose levels,
(ii) an interquartile range of glucose levels in the plurality of glucose levels,
(iii) an average squared difference of the glucose levels in the plurality of glucose levels from the mean ($\mu$) of the plurality of glucose levels ($\sigma^2$) computed as:

$$\sigma^2 = \frac{\sum_i^P (m_i - \mu)^2}{P}$$

wherein,
$m_i$ is the $i^{th}$ glucose levels in the plurality of glucose levels, and
P is the number of glucose levels in the plurality of glucose levels, and
(iv) the standard deviation of the glucose levels in the plurality of glucose levels computed as $\sqrt{\sigma^2}$.

11. The device of embodiment 2, wherein the first glycaemic risk measure or the second glycaemic risk measure is the variability in the plurality of fasting glucose levels calculated from the plurality of glucose measurements computed as one of (i), (ii), (iii), or (iv):
(i) a range of fasting glucose levels in the plurality of fasting glucose levels,
(ii) an interquartile range of fasting glucose levels in the plurality of fasting glucose levels,
(iii) an average squared difference of the fasting glucose levels in the plurality of fasting glucose levels from the mean ($\mu$) of the plurality of fasting glucose levels ($\sigma^2$) computed as:

$$\sigma^2 = \frac{\sum_i^P (m_i - \mu)^2}{P}$$

wherein,
$m_i$ is the $i^{th}$ fasting glucose levels in the plurality of fasting glucose levels, and
P is the number of fasting glucose levels in the plurality of fasting glucose levels, and
(iv) the standard deviation of the fasting glucose levels in the plurality of fasting glucose levels computed as $\sqrt{\sigma^2}$.

12. The device of embodiment 1, wherein the method further comprises:
autonomously obtaining a third data set (246), the third data set comprising one or more physiological measurements (247) of the subject; and
the fasting blood glucose target function is based upon at least the first glycaemic risk measure and a second glycaemic risk measure, wherein the first glycaemic risk measure and the second glycaemic risk measure are each independently:
(i) the total glucose level variability observed across the plurality of glucose measurements,
(ii) the variability in the plurality of fasting glucose levels calculated from the plurality of glucose measurements,
(iii) the minimum glucose measurement observed in the plurality of glucose measurements, or
(iv) the one or more physiological measurements of the subject.

13. The device of embodiment 2, wherein the method further comprises:
autonomously obtaining a third data set, the third data set comprising one or more physiological measurements of the subject; and
the fasting blood glucose target function is based upon at least the first glycaemic risk measure, the second glycaemic risk measure and a third glycaemic risk measure, wherein the first glycaemic risk measure, the second glycaemic risk measure, and the third glycaemic risk measure are each independently:
(i) the total glucose level variability observed across the plurality of glucose measurements,
(ii) the variability in the plurality of fasting glucose levels calculated from the plurality of glucose measurements,
(iii) the minimum glucose measurement observed in the plurality of glucose measurements,
(iv) the rate of change in an insulin sensitivity factor calculated using the plurality of glucose measurements and the second data set,
(v) the basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course; or (vi) the one or more physiological measurements of the subject.

14. The device of embodiment 12 or 13, wherein each physiological measurement in the one or more physiological measurements is a body temperature of the subject or a measurement of cardiovascular activity of the subject.

15. A method for autonomously adjusting a long acting insulin medicament dosage in a prescribed insulin regimen for a subject, the method comprising:

obtaining a first data set (228), the first data set comprising a plurality of glucose measurements of the subject taken over a time course and, for each respective glucose measurement (230) in the plurality of glucose measurements, a corresponding timestamp (232) representing when in the time course the respective glucose measurement was made;

updating a first glycaemic risk measure (236), wherein the first glycaemic risk measure is:
(i) a total glucose level variability observed across the plurality of glucose measurements,
(ii) a variability in a plurality of fasting glucose levels calculated from the plurality of glucose measurements, or
(iii) a minimum glucose measurement observed in the plurality of glucose measurements; and computing a fasting blood glucose target function that is based upon the first glycaemic risk measure thereby obtaining an updated target fasting blood glucose level that is between a minimum target fasting blood glucose level (226) and a maximum target fasting blood glucose level (227); and adjusting the long acting insulin medicament dosage based upon the updated target fasting blood glucose level.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIG. 1, 2, or 3 and/or described in FIG. 4. These program modules can be stored on a CD-ROM, DVD, magnetic disk storage product, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

The invention claimed is:

1. A device for autonomously adjusting a long acting insulin medicament dosage in a prescribed insulin regimen for a subject, wherein the device comprises one or more processors and a memory, the memory comprising:

a first data structure that includes the prescribed insulin regimen including a basal insulin medicament dosage regimen, wherein the basal insulin medicament dosage regimen specifies the long acting insulin medicament dosage and wherein the first data structure further comprises:
(i) a target fasting blood glucose level,
(ii) a minimum target fasting blood glucose level, and
(iii) a maximum target fasting blood glucose level, an indication as to when the subject is to inject, and instructions that, when executed by the one or more processors, perform a method of:

obtaining a first data set, the first data set comprising a plurality of glucose measurements of the subject taken over a time course and, for each respective glucose measurement in the plurality of glucose measurements, a corresponding timestamp representing when in the time course the respective glucose measurement was made;

obtaining a second data set from one or more insulin pens used by the subject to apply the prescribed insulin regimen, the second data set comprising a plurality of insulin medicament records over the time course, each insulin medicament record in the plurality of medicament records comprising:
(i) a respective insulin medicament injection event representing an insulin medicament injection into the subject using a respective insulin pen in the one or more insulin pens, and
(ii) a corresponding electronic timestamp that is automatically generated by the respective insulin pen upon occurrence of the respective insulin medicament injection event;

updating a first glycaemic risk measure, wherein the first glycaemic risk measure is:
(i) a total glucose level variability observed across the plurality of glucose measurements,
(ii) a variability in a plurality of fasting glucose levels calculated from the plurality of glucose measurements, or
(iii) a minimum glucose measurement observed in the plurality of glucose measurements;

computing a fasting blood glucose target function that is based upon at least the first glycaemic risk measure thereby obtaining an updated target fasting blood glucose level that is between the minimum target fasting blood glucose level and the maximum target fasting blood glucose level; and adjusting the long acting insulin medicament dosage based upon the updated target fasting blood glucose level, wherein the first data structure further comprises an indication as to when the subject is to inject the long acting insulin medicament dosage, and the method further comprises:

the fasting blood glucose target function is based upon at least the first glycaemic risk measure and a second glycaemic risk measure, wherein the first glycaemic risk measure and the second glycaemic risk measure are each independently:

(i) the total glucose level variability observed across the plurality of glucose measurements, (ii) the variability in the plurality of fasting glucose levels calculated from the plurality of glucose measurements, (iii) the minimum glucose measurement observed in the plurality of glucose measurements, (iv) a rate of change in an insulin sensitivity factor calculated using the plurality of glucose measurements and the second data set, or (v) a basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course.

2. The device of claim 1, wherein a range of possible values for the first glycaemic risk measure and a range of possible values for the measure are each dimensions of an N-dimensional space ($\mathbb{R}^N$) and the fasting blood glucose target function has the form:

$$\Sigma_i^{N-1} c_i x_i = FGL$$

wherein,
$c_i$ is an $i^{th}$ constant applied to an $x_i^{th}$ glycaemic risk measure, wherein the $x_i^{th}$ glycaemic risk measure is in a plurality of glycaemic risk measures that includes the first glycaemic risk measure and the second glycaemic risk measure, and wherein i is an integer between one and N−1; and
FGL is the target fasting blood glucose level.

3. The device of claim 1,
the first glycaemic risk measure is the variability in the plurality of fasting glucose levels,
the second glycaemic risk measure is the basal adherence score over the time course, and,
a range of possible values for the first glycaemic risk measure and a range of possible values for the second glycaemic risk measure are each dimensions of an N-dimensional space ($\mathbb{R}^N$) and the fasting blood glucose target function has the form:

$$c_1 x_1 + c_2 x_2 = FGL$$

wherein,
$c_1$ is a constant applied to the first glycaemic risk measure,
$c_2$ is a constant applied to the second glycaemic risk measure, and
FGL is the target fasting blood glucose level.

4. The device of claim 1, wherein
the first glycaemic risk measure is the variability in the plurality of fasting glucose levels,
the second glycaemic risk measure is the basal adherence score over the time course,
a third glycaemic risk measure is the minimum glucose measurement in the plurality of glucose measurements of the subject, and
the fasting blood glucose target function is a function of:
(i) the variability in the plurality of fasting glucose levels as a first dimension of the N-dimensional space,
(ii) the basal adherence score over the time course as a second dimension of the N-dimensional space, and
(iii) and the minimum glucose measurement in the plurality of glucose measurements of the subject as a third dimension of the N-dimensional space.

5. The device of claim 4 wherein a range of possible values for the variability in the plurality of fasting glucose levels define a first dimension a three-dimensional space ($\mathbb{R}^3$), a range of possible values for the basal adherence score over the time course define a second dimension in the three-dimensional space, and a range of possible values for the minimum glucose measurement define a third-dimension in the three dimensional space, and the fasting blood glucose target function has the form:

$$c_1 x + c_2 y + c_3 z = FGL$$

wherein,
$c_1$ is a first constant applied to the variability in the plurality of fasting glucose levels,
$c_2$ is a second constant applied to the basal adherence score over the time course,
$c_3$ is a third constant applied to the minimum glucose measurement, and
FGL is the target fasting blood glucose level.

6. The device of claim 1, wherein the method further comprises:
storing the updated target fasting blood glucose level in the first data structure and wherein
the method is repeated on a recurring basis.

7. The device of claim 1, wherein successive measurements in the plurality of glucose measurements are autonomously taken from the subject at an interval rate of 5 minutes or less, 3 minutes or less, or 1 minute or less.

8. The device of claim 1, wherein the first glycaemic risk measure or the second glycaemic risk measure is the total glucose level variability observed across the plurality of glucose measurements computed as one of (i), (ii), (iii), or (iv):
(i) a range of total glucose levels in the plurality of glucose levels,
(ii) an interquartile range of glucose levels in the plurality of glucose levels,
(iii) an average squared difference of the glucose levels in the plurality of glucose levels from the mean ($\mu$) of the plurality of glucose levels ($\sigma^2$) computed as:

$$\sigma^2 = \frac{\sum_i^P (m_i - \mu)^2}{P}$$

wherein,
$m_i$ is the $i^{th}$ glucose levels in the plurality of glucose levels, and
P is the number of glucose levels in the plurality of glucose levels, and (iv) the standard deviation of the glucose levels in the plurality of glucose levels computed as $\sqrt{\sigma^2}$.

9. The device of claim 1, wherein the method further comprises:
autonomously obtaining a third data set, the third data set comprising one or more physiological measurements of the subject; and
the fasting blood glucose target function is based upon at least the first glycaemic risk measure, the second glycaemic risk measure and a third glycaemic risk measure, wherein the first glycaemic risk measure, the second glycaemic risk measure, and the third glycaemic risk measure are each independently:

(i) the total glucose level variability observed across the plurality of glucose measurements, (ii) the variability in the plurality of fasting glucose levels calculated from the plurality of glucose measurements, (iii) the minimum glucose measurement observed in the plurality of glucose measurements, (iv) the rate of change in an insulin sensitivity factor calculated using the plurality of glucose measurements and the second data set, (v) the basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course; or (vi) the one or more physiological measurements of the subject.

10. The device of claim 1, wherein each physiological measurement in the one or more physiological measurements is a body temperature of the subject or a measurement of cardiovascular activity of the subject.

11. The device of claim 1, wherein a respective insulin medicament injection event includes an amount of insulin medicament injected into the subject using a respective insulin pen in the one or more insulin pens.

12. The device of claim 1, wherein a fasting event is deemed insulin regimen adherent when the acquired one or more medicament records establish, on a temporal and quantitative basis, adherence with the basal insulin medicament regimen during the fasting event, wherein a fasting event is deemed insulin regimen nonadherent when the acquired one or more medicament records do not include one or more medicament records that establish, on a temporal and quantitative basis, adherence with the basal insulin medicament dosage regimen during the fasting event.

13. The device of claim 1, wherein (a) the number of insulin medicament injection events that were taken by the subject when dictated by the basal insulin medicament dosage regimen corresponds to the number of adherent fasting events, and wherein (b) the total number of basal insulin medicament injection events dictated by the basal insulin medicament dosage regimen in the time course corresponds to the total number adherent and nonadherent fasting event.

14. The device of claim 1, wherein the basal insulin medicament dosage regimen specifies that a dose of long acting insulin medicament is to be taken during each respective epoch in a plurality of epochs, wherein each respective epoch is an indication, as to when the subject is to inject the long acting insulin medicament dosage, and that a fasting event is deemed insulin regimen nonadherent, when there are no medicament records for the epoch associated with the fasting event.

15. A method for autonomously adjusting a long acting insulin medicament dosage in a prescribed insulin regimen for a subject, the method comprising:

obtaining a first data set, the first data set comprising a plurality of glucose measurements of the subject taken over a time course and, for each respective glucose measurement in the plurality of glucose measurements, a corresponding timestamp representing when in the time course the respective glucose measurement was made;

obtaining a second data set from one or more insulin pens used by the subject to apply the prescribed insulin regimen, the second data set comprising a plurality of insulin medicament records over the time course, each insulin medicament record in the plurality of medicament records comprising: (i) a respective insulin medicament injection event representing an insulin medicament injection into the subject using a respective insulin pen in the one or more insulin pens and (ii) a corresponding electronic timestamp that is automatically generated by the respective insulin pen upon occurrence of the respective insulin medicament injection event;

updating a first glycaemic risk measure, wherein the first glycaemic risk measure is:

(i) a total glucose level variability observed across the plurality of glucose measurements, (ii) a variability in a plurality of fasting glucose levels calculated from the plurality of glucose measurements, or (iii) a minimum glucose measurement observed in the plurality of glucose measurements;

computing a fasting blood glucose target function that is based upon at least the first glycaemic risk measure thereby obtaining an updated target fasting blood glucose level that is between the minimum target fasting blood glucose level and the maximum target fasting blood glucose level;

adjusting the long acting insulin medicament dosage based upon the updated target fasting blood glucose level and wherein, the fasting blood glucose target function is based upon at least the first glycaemic risk measure and a second glycaemic risk measure, wherein the first glycaemic risk measure and the second glycaemic risk measure are each independently:

(i) the total glucose level variability observed across the plurality of glucose measurements, (ii) the variability in the plurality of fasting glucose levels calculated from the plurality of glucose measurements, (iii) the minimum glucose measurement observed in the plurality of glucose measurements, (iv) a rate of change in an insulin sensitivity factor calculated using the plurality of glucose measurements and the second data set, or (v) a basal adherence score over the time course that is computed by dividing (a) a number of insulin medicament injection events that were taken by the subject when dictated by the basal insulin medicament dosage regimen by (b) a total number of basal insulin medicament injection events dictated by the basal insulin medicament dosage regimen in the time course.

* * * * *

UNITED STATES PATENT AND TRADEMARK OFFICE
CERTIFICATE OF CORRECTION

| | |
|---|---|
| PATENT NO. | : 11,373,746 B2 |
| APPLICATION NO. | : 16/316237 |
| DATED | : June 28, 2022 |
| INVENTOR(S) | : Aradottir et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 842 days.

Signed and Sealed this
Eighth Day of July, 2025

Coke Morgan Stewart
*Acting Director of the United States Patent and Trademark Office*